(12) United States Patent
Nishikido et al.

(10) Patent No.: US 7,084,088 B2
(45) Date of Patent: Aug. 1, 2006

(54) LEWIS ACID CATALYST COMPOSITION

(75) Inventors: Joji Nishikido, Tokyo (JP); Akihiro Yoshida, Tokyo (JP); Masanori Ikeda, Fuji (JP)

(73) Assignees: The Noguchi Institute, Tokyo (JP); Asahi Kasei Kabushiki Kaisha, Osaka (JP)

( * ) Notice: Subject to any disclaimer, the term of this patent is extended or adjusted under 35 U.S.C. 154(b) by 5 days.

(21) Appl. No.: 10/491,532

(22) PCT Filed: Dec. 19, 2002

(86) PCT No.: PCT/JP02/13302

§ 371 (c)(1),
(2), (4) Date: Apr. 2, 2004

(87) PCT Pub. No.: WO03/051511

PCT Pub. Date: Jun. 26, 2003

(65) Prior Publication Data

US 2004/0242411 A1 Dec. 2, 2004

(30) Foreign Application Priority Data

Dec. 19, 2001 (JP) .............................. 2001-386050
Oct. 3, 2002 (JP) .............................. 2002-290745

(51) Int. Cl.
*B01J 31/00* (2006.01)
(52) U.S. Cl. .................... 502/155; 502/152; 502/103
(58) Field of Classification Search ................ 502/155, 502/152, 103
See application file for complete search history.

(56) References Cited

U.S. PATENT DOCUMENTS

| | | |
|---|---|---|
| 5,463,082 A | 10/1995 | Horvath et al. |
| 6,245,706 B1 * | 6/2001 | Hlatky ........................ 502/152 |
| 6,436,866 B1 | 8/2002 | Nishikido et al. |
| 6,610,789 B1 * | 8/2003 | Watakabe et al. ............ 525/276 |
| 6,617,474 B1 * | 9/2003 | Favre et al. ................. 568/451 |
| 6,727,329 B1 * | 4/2004 | Vogel ........................ 526/127 |

FOREIGN PATENT DOCUMENTS

| | | |
|---|---|---|
| JP | 2001-39896 A | 2/2001 |
| JP | 2001-190962 A | 7/2001 |
| JP | 2002-320858 A | 11/2002 |

OTHER PUBLICATIONS

International Search Report and English translation thereof.
Mikami et al., Lewis acid catalysis by lanthanide complexes with tris (perfluorooctane—sulfonyl) methide ponytails in fluorous recyclable phase, Tetrahedron Letters, Jan. 18, 2001, vol. 42, No. 2, pp. 289 to 292.
Nishikido et al., The Chemical Society of Japan Koen Yokoshu, Mar. 28, 2001, vol. 79, No. 2, p. 1144.
Nishikido et al., The Chemical Society of Japan Koen Yokoshu, Sep. 20, 2001 vol. 80, p. 20.
Kaku et al., The Chemical Society of Japan Koen Yokoshu, Mar. 26, 2002, vol. 81, No. 2, p. 1193.
Mikami et al., Tetrahedron, May 13, 2002, vol. 58, No. 20, pp. 4015 to 4021.
Mikami et al., Chemistry, Jul. 2, 2002, vol. 57, No. 7, pp. 22-26.

* cited by examiner

*Primary Examiner*—J. A. Lorengo
*Assistant Examiner*—Jennine Brown
(74) *Attorney, Agent, or Firm*—Birch, Stewart, Kolasch & Birch, LLP

(57) ABSTRACT

A Lewis acid catalyst composition comprising a specific mixed medium and a Lewis acid catalyst, wherein the Lewis acid catalyst is at least one compound selected from the group consisting of compounds respectively represented by the following formulae (1) and (2):

$$[(R_f^1 SO_2)(R_f^2 SO_2)N]_n M, \quad (1)$$

and $$[(R_f^1 SO_2)(R_f^2 SO_2)(R_f^3 SO_2)C]_n M. \quad (2)$$

A method for continuously performing a reaction which proceeds in the presence of the above-mentioned Lewis acid catalyst by using a specific mixed medium and the above-mentioned Lewis acid catalyst. A novel Lewis acid catalyst.

14 Claims, No Drawings

US 7,084,088 B2

LEWIS ACID CATALYST COMPOSITION

BACKGROUND OF THE INVENTION

1. Field of the Invention

The present invention relates to a Lewis acid catalyst composition. More particularly, the present invention is concerned with a Lewis acid catalyst composition comprising a specific mixed medium and a Lewis acid catalyst which is a compound comprising a specific ligand, wherein the ligand contains a substituent selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative of the above-mentioned $C_7$–$C_{20}$ hydrocarbon group. The Lewis acid catalyst composition of the present invention exhibits high catalytic activity by virtue of its improved solubility. By the use of the Lewis acid catalyst composition of the present invention for a Lewis acid-catalyzed reaction, after the reaction, not only can the Lewis acid catalyst be easily separated and recovered from the catalytic reaction mixture containing the same, but also the recycling of the Lewis acid catalyst can be performed without suffering the lowering of the catalytic activity. The present invention is also concerned with a method for continuously performing a reaction which proceeds in the presence of the above-mentioned Lewis acid catalyst by using the above-mentioned specific mixed solvent and the Lewis acid catalyst. Further, the present invention is also concerned with a novel Lewis acid catalyst.

2. Prior Art

A Lewis acid catalyst has been employed in various acid-catalyzed reactions for the synthesis of organic compounds. However, known Lewis acid catalysts, such as aluminum chloride, boron trifluoride and titanium tetrachloride, has problems in that the catalytic reaction systems are only limited to those in which the reactions proceed stoichiometrically and those in which the types of reaction solvents used are limited.

As a Lewis acid compound, a metal salt of a sulfonylimide or sulfonylmethide comprising a fluorine-substituted compound essentially having a polymerization-active species is disclosed in Canadian Patent No. 2,236,196 and this Lewis acid compound is used as a raw material for a membrane of a fuel cell. Further, an alkali metal salt or alkaline earth metal salt of a sulfonylimide or sulfonylmethide comprising a perfluoroalkyl group is disclosed in International Patent Application Publication No. WO 99/45048. In addition, an alkali metal salt or alkaline earth metal salt of a fluorine-substituted compound comprising a carbon-carbon double bond is disclosed in U.S. Pat. No. 5,463,005. A metal salt of a sulfonylimide comprising a perfluoroalkyl group is disclosed in Japanese Patent Application prior-to-examination Publication (Tokuhyo) No. 2001-526451. However, none of the above-mentioned patent documents describe that the metal salts disclosed therein, which are Lewis acid compounds, can be used as excellent Lewis acid catalysts having high catalytic activity. Further, these patent documents have no description about a Lewis acid catalyst composition which uses the Lewis acid compound and a fluorinated compound medium in combination.

Recently, Unexamined Japanese Patent Application Publication Nos. Hei 7-246338 and Hei 10-230167 disclose that a metal salt of a bis(perfluoroalkanesulfonyl)imide is an excellent Lewis acid catalyst having high catalytic activity. Further, Unexamined Japanese Patent Application Publication No. 2000-219692 discloses that a tris(perfluoroalkanesulfonyl)methide is an excellent Lewis acid catalyst.

In general, organometal complex catalysts are used so as to catalyze reactions which proceed in a homogeneous reaction system and, therefore, the use of such catalysts in the catalytic reaction system has a problem in that, in the commercial practice of the catalytic reaction, after the reaction, the separation and recovery of the catalyst from the reaction mixture and the recycling of the recovered catalyst are accompanied with difficulties.

For solving such a problem, a number of proposals have been made with respect to methods for separating and recovering a Lewis acid catalyst employed in a reaction. As an example of the methods, there can be mentioned a method in which a Lewis acid catalyst is immobilized. For example, a study has been made about the method which comprises fixing a catalyst to an inorganic or macromolecular carrier to thereby obtain an immobilized catalyst, and effecting a solid phase synthetic reaction by dispersing the obtained immobilized catalyst in the reaction system.

Although the immobilized catalyst can be easily recovered from the synthetic reaction system, the solid phase synthetic reaction has problems in that not only is the catalytic activity lowered, but also the solid phase synthetic reaction is not applicable to all of the organic syntheses which are generally conducted in a homogeneous liquid phase. Therefore, it has been desired to develop a technique which is advantageous not only in that a reaction efficiency in a liquid phase is increased, and a post-treatment of the reaction mixture can be done simply, but also in that the catalyst used can be easily recovered and recycled. It has especially been desired to develop a method for separation, recovery and recycling of a Lewis acid catalyst, which can be widely used for various acid-catalyzed reactions.

In this situation, in Unexamined Japanese Patent Application Publication No. 2001-190962, the present inventors disclosed a Lewis acid catalyst composition for use in an acid-catalyzed reaction. In this patent document, a Lewis acid-catalyzed reaction is performed in a mixed medium comprising a perfluorinated hydrocarbon and a non-fluorinated hydrocarbon and, then, the Lewis acid catalyst is recovered and recycled by the phase separation of the resultant reaction mixture. Although this method enables the recovery and recycling of the used catalyst, this method has the following problems. When a Lewis acid catalyst reaction is performed using the Lewis acid catalyst composition of the above-mentioned patent document, due to the relatively low rate of phase separation of the reaction mixture, a lowering of the productivity is caused, so that complicated apparatuses become necessary for performing the reaction in a continuous manner, and costs for the apparatuses become high. Therefore, it has been desired to develop a Lewis acid catalyst composition and a Lewis acid catalyst which are advantageous from the viewpoint of improvement in not only the recovery of the used catalyst, but also the yield of the reaction product.

SUMMARY OF THE INVENTION

In this situation, with a view toward solving the above-mentioned problems, the present inventors have conducted extensive and intensive studies about the mutual behaviors of raw materials, a Lewis acid catalyst, a reaction medium and a reaction product in a reaction system containing these substances. As a result, it has unexpectedly been found that, when an acid-catalyzed reaction is performed using a specific Lewis acid catalyst composition which comprises a Lewis acid catalyst containing a specific substituent and a mixed medium comprising a specific fluorinated compound medium and a specific non-fluorinated compound medium, the Lewis acid catalyst exhibits high catalytic activity by virtue of its improved solubility in the fluorinated compound medium. Further, the resultant reaction mixture can separate rapidly into a catalyst phase having the catalyst dissolved therein and a product phase having a reaction product dissolved therein and, therefore, the Lewis acid catalyst can be easily recovered on one hand, and the catalyst recovery ratio can be improved on the other hand. The present inventors have also found that, by virtue of its very high phase separation rate, the above-mentioned Lewis acid catalyst composition can be advantageously used so as to perform a continuous reaction.

On the other hand, in the course of the above-mentioned study, the present inventors have also found a novel Lewis acid catalyst having high solubility in a fluorinated compound medium and having high catalytic activity as compared to those of the conventional Lewis acid catalysts.

Accordingly, it is an object of the present invention to provide a Lewis acid catalyst composition which, when used for effecting a reaction in the presence of a raw material or raw materials, enables a catalyst and a reaction product to be easily separated and recovered from the resultant reaction mixture, so that the recycling of the catalyst becomes possible.

It is another object of the present invention to provide a method for continuously performing a reaction which proceeds in the presence of a Lewis acid catalyst.

It is still another object of the present invention to provide a novel Lewis acid catalyst which has high stability in water and has high catalytic activity as compared to those of the conventional Lewis acid catalysts, and which can be widely used for various acid-catalyzed reactions.

The foregoing and other objects, features and advantages of the present invention will be apparent to those skilled in the art from the following detailed description and the appended claims.

DETAILED DESCRIPTION OF THE INVENTION

In one aspect of the present invention, there is provided a Lewis acid catalyst composition comprising a mixed medium and a Lewis acid catalyst, the mixed medium comprising (A) a fluorinated compound medium and (B) a non-fluorinated compound medium, the Lewis acid catalyst being at least one compound selected from the group consisting of compounds respectively represented by the following formulae (1) and (2):

$$[(R_f^1SO_2)(R_f^2SO_2)N]_nM \qquad (1),$$

and

$$[(R_f^1SO_2)(R_f^2SO_2)(R_f^3SO_2)C]_nM \qquad (2)$$

wherein:

each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is the substituent ($\beta$) and, in formula (2) above, at least one member selected from the group consisting of $R_f^1$ to $R_f^3$ is the substituent ($\alpha$), wherein, in the partially substituted derivative in the definition of each of the substituents ($\alpha$) and ($\beta$), a part of the fluorine atoms in the perfluorinated hydrocarbon group is replaced by at least one member selected from the group consisting of a hydrogen atom and a halogen atom exclusive of a fluorine atom, provided that, in each of the substituents ($\alpha$) and ($\beta$), a part of the fluorine atoms bonded to a carbon atom directly bonded to the —SO$_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M.

For an easy understanding of the present invention, the essential features and various preferred embodiments of the present invention are enumerated below.

1. A Lewis acid catalyst composition comprising a mixed medium and a Lewis acid catalyst, the mixed medium comprising (A) a fluorinated compound medium and (B) a non-fluorinated compound medium, the Lewis acid catalyst being at least one compound selected from the group consisting of compounds respectively represented by the following formulae (1) and (2):

$$[(R_f^1SO_2)(R_f^2SO_2)N]_nM \qquad (1),$$

and

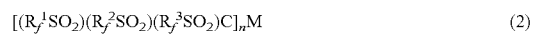
$$[(R_f^1SO_2)(R_f^2SO_2)(R_f^3SO_2)C]_nM \qquad (2)$$

wherein:

each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is the substituent ($\alpha$) and, in formula (2) above, at least one member selected from the group consisting of $R_f^1$ to $R_f^3$ is the substituent ($\alpha$), wherein, in the partially substituted derivative in the definition of each of the substituents ($\alpha$) and ($\beta$), a part of the fluorine atoms in the perfluorinated hydrocarbon group is replaced by at least one member selected from the group consisting of a hydrogen atom and a halogen atom exclusive of a fluorine atom, provided that, in each of the substituents ($\alpha$) and ($\beta$), a part of the fluorine atoms bonded to a carbon atom directly bonded to the —SO$_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M.

2. The Lewis acid catalyst composition according to item 1 above, wherein each of $R_f^1$ to $R_f^3$ in the formulae (1) and (2) independently represents substituent ($\alpha$) which is represented by any one of the following formulae (3) and (4):

$$CF_2X^1CFX^2\text{—}[OCF_2CF(CF_3)]_t\text{—}O\text{—}[CF_2]_u\text{—} \qquad (3),$$

and $$CF_2\text{=}CF\text{—}[OCF_2CF(CF_3)]_t\text{—}O\text{—}[CF_2]_u\text{—} \qquad (4)$$

wherein, each of $X^1$ and $X^2$ independently represents an atom selected from the group consisting of a halogen atom and a hydrogen atom; t is an integer of from 1 to 4; and u is an integer of from 1 to 4.

3. A method for continuously performing a reaction which proceeds in the presence of a Lewis acid catalyst, which comprises:

providing a reaction zone containing a Lewis acid catalyst and a fluorinated compound medium (A), wherein the Lewis acid catalyst is at least one compound selected from the group consisting of compounds respectively represented by the following formulae (1) and (2):

$$[(R_f^1SO_2)(R_f^2SO_2)N]_nM \qquad (1), \text{ and}$$

$$[(R_f^1SO_2)(R_f^2SO_2)(R_f^3SO_2)C]_nM \qquad (2)$$

wherein:

each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is the substituent ($\alpha$) and, in formula (2) above, at least one member selected from the group consisting of $R_f^1$ to $R_f^3$ is the substituent ($\alpha$), wherein, in the partially substituted derivative in the definition of each of the substituents ($\alpha$) and ($\beta$), a part of the fluorine atoms in the perfluorinated hydrocarbon group is replaced by at least one member selected from the group consisting of a hydrogen atom and a halogen atom exclusive of a fluorine atom, provided that, in each of the substituents ($\alpha$) and ($\beta$), a part of the fluorine atoms bonded to a carbon atom directly bonded to the —$SO_2$ group is not replaced by a hydrogen atom, M represents an atom selected from the group consisting of transition metals including rare earth metals, gallium, indium, thallium, silicon, germanium, tin, lead, antimony and bismuth, and n is an integer equivalent to the valence of M; and continuously feeding a mixture of at least one reactant and a non-fluorinated compound medium (B) and mixing the fluorinated compound medium (A) containing the Lewis acid catalyst and the non-fluorinated compound medium (B) containing at least one reactant to thereby effect a reaction in the presence of the Lewis acid catalyst and obtain a reaction mixture comprising a reaction-formed fluorinated compound medium (A) phase containing the Lewis acid catalyst and a reaction-formed non-fluorinated compound medium (B) phase containing a reaction product, while continuously separating the reaction-formed non-fluorinated compound medium (B) phase containing the reaction product from the reaction-formed fluorinated compound medium (A) phase containing the Lewis acid catalyst in a phase separation zone which is disposed in association with the reaction zone and while continuously withdrawing the reaction-formed non-fluorinated compound medium (B) phase containing the reaction product from the phase separation zone.

4. A Lewis acid catalyst which is a compound represented by the following formula (1'):

$$[(R_f^1SO_2)(R_f^2SO_2)N]_nM \qquad (1')$$

wherein:

each of $R_f^1$ and $R_f^2$ independently represents a substituent selected from the group consisting of a perfluorinated, saturated $C_9$–$C_{16}$ hydrocarbon group containing in the skeleton thereof at least one heteroatom selected from the group consisting of a nitrogen atom and an oxygen atom and a partially substituted derivative thereof, wherein, in the partially substituted derivative in the definition of the substituent, a part of the fluorine atoms in the perfluorinated hydrocarbon group is replaced by at least one member selected from the group consisting of a hydrogen atom and a halogen atom exclusive of a fluorine atom, provided that, in the substituent, a part of the fluorine atoms bonded to the carbon atom directly bonded to the —$SO_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M.

5. The Lewis acid catalyst according to item 4 above, wherein each of $R_f^1$ and $R_f^2$ in the formula (1') represents a substituent represented by the following formula (3):

$$CF_2X^1CFX^2\text{—}[OCF_2CF(CF_3)]_t\text{—}O\text{—}[CF_2]_u\text{—} \qquad (3)$$

wherein, each of $X^1$ and $X^2$ independently represents an atom selected from the group consisting of a halogen atom and a hydrogen atom; t is an integer of from 1 to 4; and u is an integer of from 1 to 4.

6. The Lewis acid catalyst according to item 4 or 5 above, wherein M in the formula (1') represents tin, and the Lewis acid catalyst is for use in catalyzing an oxidation reaction of a ketone compound by use of hydrogen peroxide.

7. The Lewis acid catalyst according to item 4 or 5 above, wherein M in the formula (1') represents tin, and the Lewis acid catalyst is for use in catalyzing a transesterification reaction.

8. The Lewis acid catalyst according to item 4 or 5 above, wherein M in the formula (1') represents hafnium, and the Lewis acid catalyst is for use in catalyzing a reaction selected from the group consisting of a carbon-carbon bond-forming reaction, a dehydration reaction and an oxidation reaction by use of hydrogen peroxide.

9. A Lewis acid catalyst which is a compound represented by the following formula (2'):

$$[(R_f^1SO_2)(R_f^2SO_2)(R_f^3SO_2)C]_nM \quad (2')$$

wherein:
each of $R_f^1$ to $R_f^3$ in the formula (2') represents a substituent represented by the following formula (3):

$$CF_2X^1CFX^2-[OCF_2CF(CF_3)]_t-O-[CF_2]_u- \quad (3)$$

wherein, each of $X^1$ and $X^2$ independently represents an atom selected from the group consisting of a halogen atom and a hydrogen atom; t is an integer of from 1 to 4; and u is an integer of from 1 to 4;
M represents an atom selected from the group consisting of transition metals including rare earth metals, gallium, indium, thallium, silicon, germanium, tin, lead, antimony and bismuth; and
n is an integer equivalent to the valence of M.

10. The Lewis acid catalyst according to item 9 above, wherein M in the formula (2') represents tin, and the Lewis acid catalyst is for use in catalyzing an oxidation reaction of a ketone compound by use of hydrogen peroxide.

11. The Lewis acid catalyst according to item 9 above, wherein M in the formula (2') represents tin, and the Lewis acid catalyst is for use in catalyzing a transesterification reaction.

12. The Lewis acid catalyst according to item 9 above, wherein M in the formula (2') represents hafnium, and the Lewis acid catalyst is for use in catalyzing a reaction selected from the group consisting of a carbon-carbon bond-forming reaction, a dehydration reaction and an oxidation reaction by use of hydrogen peroxide.

13. A Lewis acid catalyst which is at least one compound selected from the group consisting of compounds respectively represented by the following formulae (5) and (6):

$$[(R_f^1SO_2)(R_f^2SO_2)N]_nSn \quad (5), \text{ and}$$

$$[(R_f^1SO_2)(R_f^2SO_2)(R_f^3SO_2)C]_nSn \quad (6)$$

wherein:
each of $R_f^1$ to $R_f^3$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent (β) selected from the group consisting of a perfluorinated, saturated or unsaturated $C_1$–$C_{16}$ hydrocarbon group containing no heteroatom and a partially substituted derivative thereof, provided that, in formula (5) above, at least one member selected from the group consisting of $R_f^1$ and $R_f^2$ is the substituent (α) and, in formula (6) above, at least one member selected from the group consisting of $R_f^1$ to $R_f^3$ is the substituent (α),
wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —SO₂ group is not replaced by a hydrogen atom; and
n is an integer equivalent to the valence of Sn, the Lewis acid catalyst being for use in catalyzing a reaction selected from the group consisting of an oxidation reaction of a ketone compound by use of hydrogen peroxide and a transesterification reaction.

14. A Lewis acid catalyst which is at least one compound selected from the group consisting of compounds respectively represented by the following formulae (7) and (8):

$$[(R_f^1SO_2)(R_f^2SO_2)N]_nHf \quad (7),$$

and $$[(R_f^1SO_2)(R_f^2SO_2)(R_f^3SO_2)C]_nHf \quad (8)$$

wherein:
each of $R_f^1$ to $R_f^3$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent (β) selected from the group consisting of a perfluorinated, saturated or unsaturated $C_1$–$C_{16}$ hydrocarbon group containing no heteroatom and a partially substituted derivative thereof, provided that, in formula (7) above, at least one member selected from the group consisting of $R_f^1$ and $R_f^2$ is the substituent (α) and, in formula (8) above, at least one member selected from the group consisting of $R_f^1$ to $R_f^3$ is the substituent (α),
wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —SO₂ group is not replaced by a hydrogen atom; and
n is an integer equivalent to the valence of Hf, the Lewis acid catalyst being for use in catalyzing a reaction selected from the group consisting of a carbon-carbon bond-forming reaction, a dehydration reaction and an oxidation reaction by use of hydrogen peroxide.

Hereinbelow, the present invention will be described in more detail.

The Lewis acid catalyst composition of the present invention comprises a mixed medium and a Lewis acid catalyst. The Lewis acid catalyst contained in the Lewis acid catalyst composition of the present invention is at least one compound selected from the group consisting of compounds respectively represented by the following formulae (1) and (2):

$$[(R_f^1SO_2)(R_f^2SO_2)N]_nM \quad (1),$$

and $$[(R_f^1SO_2)(R_f^2SO_2)(R_f^3SO_2)C]_nM \quad (2)$$

wherein:
each of $R_f^1$ to $R_f^3$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative of the $C_7$–$C_{20}$ hydrocarbon group above, or a substituent (β) selected from the group consisting of a perfluorinated, saturated or unsaturated $C_1$–$C_{16}$ hydrocarbon group containing no heteroatom and a partially substituted derivative of the $C_7$–$C_{20}$ hydrocarbon group above, provided that, in formula (1) above, at least one member selected from the group consisting of $R_f^1$ and $R_f^2$ is the substituent (α) and, in formula (2) above, at least one member selected from the group consisting of $R_f^1$ to $R_f^3$ is the substituent (α), wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —$SO_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M.

Each of the compounds respectively represented by formulae (1) and (2) above, which are the Lewis acid catalysts contained in the Lewis acid catalyst composition of the present invention, contains at least one substituent (α). The substituent (α) is a substituent selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative of the $C_7$–$C_{20}$ hydrocarbon group above. The number of carbon atoms of substituent (α) is 7 to 20, wherein lower limit of the number of carbon atoms is preferably 8, more preferably 9, most preferably 10, and upper limit of the number of carbon atoms is preferably 18, more preferably 16, most preferably 13. When substituent (α) has 7 to 20 carbon atoms, a Lewis acid catalyst comprising such a substituent (α) is well soluble in a fluorinated compound medium (A) and is fixed therein without dissolving into a non-fluorinated compound medium (B). Therefore, after performing a reaction in the presence of such a Lewis acid catalyst, the Lewis acid catalyst used can be easily separated from the reaction system.

In addition to the substituent (α), each of the compounds respectively represented by formulae (1) and (2) above may have a substituent (β).

In addition to the substituent (α) containing a heteroatom, the compounds respectively represented by formulae (1) and (2) above may additionally have a substituent (β) selected from the group consisting of a perfluorinated, saturated or unsaturated $C_1$–$C_{16}$ hydrocarbon group containing no heteroatom and a partially substituted derivative of the $C_1$–$C_{16}$ hydrocarbon group above. The number of carbon atoms of substituent (β) is 1 to 16, wherein lower limit of the number of carbon atoms is preferably 2, more preferably 3, most preferably 4, and upper limit of the number of carbon atoms is preferably 14, more preferably 12, most preferably 10.

When the Lewis acid catalyst used in the Lewis acid catalyst composition of the present invention is a compound represented by formula (1) above, at least one member selected from the group consisting of $R_f^1$ and $R_f^2$ is the substituent (α). When the Lewis acid catalyst is a compound represented by formula (2) above, at least one member selected from the group consisting of $R_f^1$ to $R_f^3$ is the substituent (α). That is, a compound used as a Lewis acid catalyst in the Lewis acid catalyst composition of the present invention necessarily has at least one substituent (α) containing a heteroatom. Accordingly, a compound having only substituent (β) is not used as a Lewis acid catalyst in the present invention.

Further, when the Lewis acid catalyst is a compound represented by formula (1) above, it is preferred that the substituents $R_f^1$ and $R_f^2$ are not simultaneously an unsaturated perfluorinated hydrocarbon group or a partially substituted derivative thereof. When the Lewis acid catalyst is a compound represented by formula (2) above, it is preferred that the substituents $R_f^1$ to $R_f^3$ are not simultaneously an unsaturated perfluorinated hydrocarbon group or a partially substituted derivative thereof.

The "partially substituted derivative thereof" in the definition of each of the substituents (α) and (β) is a substituent in which a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —$SO_2$ group is not replaced by a hydrogen atom. A halogen atom exclusive of a fluorine atom is a chlorine atom, a bromine atom or an iodine atom, preferably a chlorine atom or a bromine atom, more preferably a chlorine atom.

The amount of the fluorine atoms substituted with a hydrogen atom or a halogen atom exclusive of a fluorine atom is preferably 40% or less, more preferably 30% or less, still more preferably 20% or less, most preferably 10% or less, based on the number of fluorine atoms contained in the corresponding perfluorinated saturated hydrocarbon group.

On the other hand, when the substituents (α) and (β) are perfluorinated unsaturated hydrocarbon groups, preferred are those which have the carbon-carbon double bond in an amount of 40% or less, more preferably 30% or less, still more preferably 20% or less, most preferably 10% or less, based on the number of fluorine atoms contained in the corresponding perfluorinated saturated hydrocarbon group.

With respect to the compounds used as a Lewis acid catalyst in the Lewis acid catalyst composition of the present invention, it is preferred that each of $R_f^1$ to $R_f^3$ in the formulae (1) and (2) independently represents substituent (α) which is represented by any one of the following formulae (3) and (4):

$$CF_2X^1CFX^2-[OCF_2CF(CF_3)]_t-O-[CF_2]_u- \quad (3),$$

and $$CF_2=CF-[OCF_2CF(CF_3)]_t-O-[CF_2]_u- \quad (4)$$

wherein, each of $X^1$ and $X^2$ independently represents an atom selected from the group consisting of a halogen atom and a hydrogen atom; t is an integer of from 1 to 4; and u is an integer of from 1 to 4, preferably from 2 to 4, more preferably from 2 to 3.

The compounds having a specific structure represented by the formula (3) or (4) above are well soluble in a fluorinated compound medium (A) and, therefore, exhibit high catalytic activity, as compared to known Lewis acid catalysts (for example, aluminum chloride, titanium tetrachloride and boron trifluoride).

With respect to the compounds respectively represented by formula (1) and (2) above, it is preferred that each of $R_f^1$ to $R_f^3$ has 7 to 16 carbon atoms, more preferably 9 to 16 carbon atoms.

Specific examples of the substituent (α) containing at least one heteroatom include:
—$CF_2CHFCF_2OC_4F_9$, —$C_4F_8N(C_4F_9)_2$,
—$CF_2CF_2OCF(CF_3)CF_2OCF=CF_2$,
—$CF_2CF_2OCF(CF_3)CF_2OCF(CF3)CF_2OCF=CF_2$,
—$CF_2CF_2OCF(CF_3)CF_2OCHFCF_3$,
—$CF_2CF_2OCF(CF_3)CF_2OCF(CF_3)CF_2OCHFCF_3$,
—$CF_2CF_2O$—$CF(CF_3)$—$CF_2$—$OCF(CF_3)$—$CF_2OCF_2CF_3$,
—$CF_2CF_2OCF(CF_3)CF_2OCFClCF_3$ and
—$CF_2CF_2OCF(CF_3)CF_2OCFClCF_2Cl$.

Specific examples of the substituent (β) include a trifluoromethyl group, a perfluoroethyl group, a perfluoropropyl group, a perfluorobutyl group, a perfluoropentyl group, a perfluorohexyl group, a perfluoroheptyl group, a perfluorooctyl group, a perfluorononyl group, a perfluorodecyl group, a perfluoroundecyl group, a perfluorododecyl group, a perfluorotridecyl group, a perfluorotetradecyl group, a perfluoropentadecyl group and a perfluorohexadecyl group.

When the Lewis acid catalyst contained in the Lewis acid catalyst composition of the present invention is a compound represented by formula (1) above, the total number of carbon atoms of $R_f^1$ and $R_f^2$ is preferably 14 to 32, wherein lower limit of the number of carbon atoms is more preferably 16, still more preferably 18, most preferably 20, and upper limit of the number of carbon atoms is more preferably 26, most preferably 23.

When the Lewis acid catalyst contained in the Lewis acid catalyst composition of the present invention is a compound represented by formula (2) above, the total number of carbon atoms of $R_f^1$, $R_f^2$ and $R_f^3$ is preferably 21 to 48, wherein lower limit of the number of carbon atoms is more preferably 23, still more preferably 25, most preferably 27, and upper limit of the number of carbon atoms is more preferably 38, most preferably 34.

In the formulae (1) and (2) above, M represents an atom selected from the group consisting of transition metals including rare earth metals, gallium, indium, thallium, silicon, germanium, tin, lead, antimony and bismuth. With respect to the compound used as a Lewis acid catalyst in the present invention, rare earth metals, hafnium, bismuth, tin and gallium are preferred, and scandium, ytterbium, lanthanum, yttrium, hafnium, bismuth, tin and gallium are more preferred.

The below-mentioned Lewis acid catalysts of the present invention may be advantageously used as a Lewis acid catalyst in the Lewis acid catalyst composition of the present invention.

The mixed medium contained in the Lewis acid catalyst composition of the present invention comprises a fluorinated compound medium (A) and a non-fluorinated compound medium (B). The examples of such fluorinated compound medium (A) used in the present invention include a perfluorinated, saturated or unsaturated hydrocarbon and a perfluorinated, saturated or unsaturated hydrocarbon containing in the skeleton thereof at least one heteroatom selected from the group consisting of a nitrogen atom and an oxygen atom. When the perfluorinated hydrocarbon contains in the skeleton thereof a carbon-carbon double bond, an oxygen atom and/or a nitrogen atom, the total number of the carbon-carbon double bond, the oxygen atom and the nitrogen atom is preferably 40% or less, more preferably 30% or less, still more preferably 20% or less, most preferably 10% or less, based on the number of fluorine atoms contained in a corresponding perfluorinated saturated hydrocarbon.

With respect to the perfluorinated compound used as the fluorinated compound medium (A), there is no particular limitation as long as the perfluorinated compound is in a liquid form at room temperature. The perfluorinated compound medium (A) has preferably 6 to 30 carbon atoms, more preferably 6 to 20 carbon atoms, most preferably 6 to 15 carbon atoms.

Specific examples of perfluorinated saturated compounds used as the fluorinated compound medium (A) include perfluorohexane, perfluoroheptane, perfluorooctane, perfluorononane, perfluorodecane, perfluoroundecane, perfluorododecane, perfluorocyclohexane, perfluoromethylcyclohexane, perfluorodecalin and perfluoromethyldecalin.

Specific examples of perfluorinated compounds having in the skeleton thereof at least one member selected from the group consisting of an oxygen atom, a nitrogen atom and a carbon-carbon double bond include perfluoro-2-butyltetrahydrofuran, perfluorotributylamine, perfluorotriethylamine, perfluoro-5-methyl-3,6-dioxanonane, 2H-perfluoro-5-methyl-3,6-dioxanonane, perfluoro-2,3,5-trimethylhexene and a low molecular weight polymer of hexafluoropropylene oxide.

As the fluorinated compound medium (A), these media can be used individually or in combination.

With respect to the non-fluorinated compound medium (B), there is no particular limitation as long as the non-fluorinated compound medium (B) is in a liquid form at room temperature and it can be phase-separated from the fluorinated compound medium (A). Examples of the non-fluorinated compound medium (B) include an alicyclic hydrocarbon and an aliphatic hydrocarbon; a halogenated aliphatic hydrocarbon exclusive of a fluorinated aliphatic hydrocarbon; an aromatic hydrocarbon; a halogenated aromatic hydrocarbon exclusive of a fluorinated aromatic hydrocarbon; an ester compound and an ether compound.

With respect to the aliphatic hydrocarbon used as a non-fluorinated compound medium (B), those which have 5 to 20 carbon atoms, preferably 5 to 16 carbon atoms, can be used. Preferred are linear or branched hydrocarbons having 8 to 16 carbon atoms. Alicyclic hydrocarbons having 5 to 16 carbon atoms are also preferred. Specific examples of such aliphatic or alicyclic hydrocarbons include n-heptane, n-octane, n-nonane, n-decane, n-dodecane, n-hexadecane, cyclopentane, cyclohexane and methylcyclohexane.

With respect to the halogenated aliphatic hydrocarbon exclusive of a fluorinated aliphatic hydrocarbon, there is no particular limitation with respect to the number of carbon atoms and the number of hydrogen atoms replaced by halogen atoms as long as the halogenated aliphatic hydrocarbon is in a liquid form at room temperature. However, $C_1$–$C_{10}$ halogenated aliphatic hydrocarbons are preferred. Specific examples of such halogenated aliphatic hydrocarbons include dichloromethane, dichloroethane and dibromoethane.

With respect to the aromatic hydrocarbon used as a non-fluorinated compound medium (B), those which have 6 to 15 carbon atoms are preferred. Specific examples of such aromatic hydrocarbons include benzene and benzene substituted with an alkyl group or groups, such as toluene, o-xylene, m-xylene, p-xylene and ethylbenzene.

With respect to the halogenated aromatic hydrocarbon exclusive of a fluorinated aromatic hydrocarbon, there is no particular limitation with respect to the number of hydrogen atoms replaced by halogen atoms. However, $C_6$–$C_{10}$ halogenated aromatic hydrocarbons are preferred. Specific examples of such halogenated aromatic hydrocarbons include chlorobenzene, dichlorobenzene, bromobenzene and chlorotoluene.

With respect to the ester compound used as a non-fluorinated compound medium (B), those which have 5 to 20 carbon atoms exclusive of the carbon atoms of the carbonyl group thereof, can be used. Preferred are ester compounds corresponding to a saturated hydrocarbon having 5 to 16 carbon atoms. More preferred are ester compounds corresponding to a linear, branched or cyclic saturated hydrocarbon or an aromatic hydrocarbon having 6 or more carbon atoms, more preferably 7 to 16 carbon atoms. Specific examples of such ester compounds include n-butyl acetate, iso-butyl acetate, tert-butyl acetate, n-pentyl acetate, iso-pentyl acetate, n-hexyl acetate, n-heptyl acetate, n-octyl acetate, n-nonyl acetate, n-decyl acetate, n-dodecyl acetate, cyclohexyl acetate, benzyl acetate, n-butyl propionate, iso-butyl propionate, tert-butyl propionate, n-pentyl propionate, iso-pentyl propionate, n-hexyl propionate, n-heptyl propionate, n-octyl propionate, n-nonyl propionate, n-decyl propionate, n-dodecyl propionate, cyclohexyl propionate, benzyl propionate, n-propyl butyrate, n-butyl butyrate, iso-butyl butyrate, tert-butyl butyrate, n-pentyl butyrate, iso-pentyl butyrate, n-hexyl butyrate, n-heptyl butyrate, n-octyl butyrate, n-nonyl butyrate, n-decyl butyrate, n-dodecyl butyrate, cyclohexyl butyrate, methyl benzoate, ethyl benzoate and propyl benzoate.

With respect to the ether compound used as a non-fluorinated compound medium (B), ether compounds corresponding to linear or branched saturated hydrocarbons having 3 to 15 carbon atoms can be used. Preferred are ether compounds corresponding to hydrocarbons having 4 or more carbon atoms, more preferably 6 to 15 carbon atoms. In addition, use can be made of cyclic ether compounds having 4 or more carbon atoms and ether compounds corresponding to aromatic hydrocarbons having 6 or more carbon atoms. Specific examples of such ether compounds include dipropyl ether, tert-butyl methyl ether, dibutyl ether, dipentyl ether, dihexyl ether, diheptyl ether, dioctyl ether, dioxane, furan and anisole.

These non-fluorinated compound media (B) can be used individually or in combination.

Next, an explanation is made with respect to the formulation of the Lewis acid catalyst composition of the present invention.

The volume ratio of the fluorinated compound medium (A) to the non-fluorinated compound medium (B) ((A):(B)) is preferably from 5:95 to 95:5, more preferably from 10:90 to 90:10, most preferably 30:70 to 70:30. When the Lewis acid catalyst composition of the present invention is used for performing an acid-catalyzed reaction, a raw material for the reaction can be also used as a non-fluorinated compound (B).

With respect to the amount of the mixed medium (total amount of the fluorinated compound medium (A) and the non-fluorinated compound medium (B) in the Lewis acid catalyst composition), the weight ratio of the mixed medium to the Lewis acid catalyst is preferably not less than 1, more preferably from 2 to 100,000, still more preferably from 2 to 10,000, most preferably from 5 to 1,000. When the Lewis acid catalyst composition of the present invention is used for acid-catalyzed reactions, the molar ratio of the Lewis acid catalyst to the raw material is in the range of from 0.0001 to 10, preferably from 0.001 to 1.

When an acid-catalyzed reaction is performed using the Lewis acid catalyst composition of the present invention, the reaction temperature is generally 200° C. or lower, preferably from −10 to 170° C., more preferably from 0 to 140° C. In the present invention, the reaction time varies depending on the type of the Lewis acid catalyst, the amount of the Lewis acid catalyst (relative to the amount of the raw material), and the reaction temperature; however, a period of time of from several minutes to 72 hours is generally preferred.

Hereinbelow, an explanation is made with respect to a method for recovering the Lewis acid catalyst after performing an acid-catalyzed reaction using the Lewis acid catalyst composition of the present invention.

The Lewis acid catalyst used in the present invention is a specific, polar segment-containing metal complex and, therefore, the Lewis acid catalyst is well soluble in the fluorinated compound medium (A) and forms a homogeneous solution. As a consequence, when an acid-catalyzed reaction is performed with the Lewis acid catalyst composition of the present invention, the reaction yield becomes improved. A reaction mixture obtained after the reaction comprises a reaction-formed fluorinated compound medium (A) phase containing the Lewis acid catalyst and the reaction-formed non-fluorinated compound medium (B) phase containing a reaction product. Due to a phase separation between these phases in the reaction mixture, the reaction-formed non-fluorinated compound medium (B) phase containing a reaction product and the reaction-formed fluorinated compound medium (A) phase containing the Lewis acid catalyst are caused to form an upper phase and a lower phase, respectively. This phase separation takes not more than 10 seconds. Such a rapid phase separation rate not only is very advantageous for the commercial practice of the catalytic reaction which involves a process for the separation and recovery of the catalyst from the reaction system, but also improves the catalyst recovery ratio and enables the use of simplified apparatuses.

In general, it is preferred that a raw material of a Lewis acid-catalyzed reaction performed using the Lewis acid composition of the present invention is a nucleophilic reagent. In the present invention, the term "nucleophilic reagent" means a compound which has an affinity to a cation present in the Lewis acid and which is capable of coordinating to the cation. As an example of such a nucleophilic reagent, a compound which contains an element, such as oxygen or nitrogen, can be mentioned. Examples of nucleophilic reagents include ketones, aldehydes, nitriles, ketenes, acid anhydrides, acid halides, esters, thioesters, lactones, ethers, alcohols, phenols, carboxylic acids and nitro compounds. As another example of the nucleophilic reagent, an unsaturated hydrocarbon can be mentioned, wherein the unsaturated hydrocarbon has an affinity to a cation present in the Lewis acid and is capable of coordinating to the cation. Examples of such unsaturated hydrocarbons include nucleophilic olefins.

The Lewis acid catalyst composition of the present invention can be used for performing a reaction which uses the above-mentioned compound or compounds as a raw material or raw materials. The Lewis acid catalyst composition can be employed in reactions, such as the Diels-Alder reaction; the Michael reaction; the Friedel-Crafts reaction; a synthetic reaction of a Schiff base; the Fries rearrangement reaction; a methylolation reaction of a benzene nucleus; the Meerwein-Ponndorf-Verley reduction reaction; an aldol reaction; an esterification reaction; a transesterification reaction; the Mannich reaction; an oxidation reaction with hydrogen peroxide, an organic peroxide or molecular oxygen; a dehydration reaction of an alcohol; an O-glycosidation reaction; and a polymerization reaction of an olefin.

As explained in detail above, after performing an acid-catalyzed reaction with the Lewis acid catalyst composition of the present invention, the Lewis acid catalyst and a reaction product contained in the resultant reaction mixture may be separated from each other within a short period of time as short as 10 seconds or less. By virtue of this excellent property, the Lewis acid catalyst composition of the present invention can be used for performing a reaction in not only a batch-wise manner, but also a continuous manner. Accordingly, the present invention provides a method for continuously performing a reaction which proceeds in the presence of a Lewis acid catalyst, which comprises:

providing a reaction zone containing a Lewis acid catalyst and a fluorinated compound medium (A), wherein the Lewis acid catalyst is at least one compound selected from the group consisting of compounds respectively represented by the following formulae (1) and (2):

(1), and

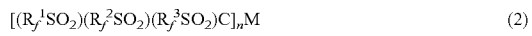

(2)

wherein:
each of $R_f^1$ to $R_f^2$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent (β) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is the substituent (α) and, in formula (2) above, at least one member selected from the group consisting of $R_f^1$ to $R_f^3$ is the substituent (α), wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —$SO_2$ group is not replaced by a hydrogen atom, M represents an atom selected from the group consisting of transition metals including rare earth metals, gallium, indium, thallium, silicon, germanium, tin, lead, antimony and bismuth, and n is an integer equivalent to the valence of M; and continuously feeding a mixture of at least one reactant and a non-fluorinated compound medium (B) and mixing the fluorinated compound medium (A) containing the Lewis acid catalyst and the non-fluorinated compound medium (B) containing at least one reactant to thereby effect a reaction in the presence of the Lewis acid catalyst and obtain a reaction mixture comprising a reaction-formed fluorinated compound medium (A) phase containing the Lewis acid catalyst and a reaction-formed non-fluorinated compound medium (B) phase containing a reaction product, while continuously separating the reaction-formed non-fluorinated compound medium (B) phase containing the reaction product from the reaction-formed fluorinated compound medium (A) phase containing the Lewis acid catalyst in a phase separation zone which is disposed in association with the reaction zone and while continuously withdrawing the reaction-formed non-fluorinated compound medium (B) phase containing the reaction product from the phase separation zone.

With respect to the Lewis acid catalyst, fluorinated compound medium (A) and non-fluorinated compound medium (B) used in the method of the present invention for continuously performing a reaction, use is made of the compounds described in connection with the Lewis acid catalyst composition of the present invention.

In the method for continuously performing a reaction which proceeds in the presence of a Lewis acid catalyst, a fluorinated compound medium (A) containing a Lewis acid catalyst forms a stationary phase and a non-fluorinated compound medium (B) containing a raw material or raw materials (reactant or reactants) forms a mobile phase. The reaction is performed by contacting the stationary phase with the mobile phase, to thereby obtain a reaction mixture comprising a reaction-formed fluorinated compound medium (A) phase containing the Lewis acid catalyst and a reaction-formed non-fluorinated compound medium (B) phase containing a reaction product. After the reaction, the reaction-formed non-fluorinated compound medium (B) phase (i.e., mobile phase) containing the reaction product is phase-separated from the reaction-formed fluorinated compound medium (A) phase (i.e., stationary phase) containing the Lewis acid catalyst, and only the mobile phase is recovered, thereby obtaining the desired reaction product easily. The fluorinated compound medium (A) phase which is the stationary phase remaining in the reaction zone can be reused for performing the reaction. The phase separation is performed in a phase separation zone, and the phase separation zone can be provided inside the reactor (in this case, the reactor provides both the reaction zone and the phase separation zone) or, alternatively, the phase separation zone can be a phase separation apparatus provided separately from the reactor used as the reaction zone. In the method of the present invention, a reaction-formed fluorinated compound medium (A) phase containing the Lewis acid catalyst and a reaction-formed non-fluorinated compound medium (B) phase containing a reaction product can be phase separated very rapidly within 10 seconds. By virtue of this excellent property, a reaction which proceeds in the presence of a Lewis acid catalyst can be performed continuously without using a complicated apparatus or repeating a phase separation operation and, hence, the continuous reactions can be performed easily without a need of cumbersome operations.

For example, when a tubular reactor (a reaction column) is used as a reaction zone, a fluorinated compound medium (A) containing a Lewis acid catalyst (i.e., a stationary phase) is charged into the reactor. A non-fluorinated compound medium (B) containing a reactant (i.e., a mobile phase) is continuously charged into the stationary phase in the reactor from the bottom of the stationary phase while mixing the fluorinated compound medium (A) containing the Lewis acid catalyst and the non-fluorinated compound medium (B) containing the reactant, to thereby effect a reaction in the presence of the Lewis acid catalyst. During the reaction, the non-fluorinated compound medium (B) containing the reactant gets in contact with the fluorinated compound medium (A) containing the Lewis acid catalyst which is positioned above the non-fluorinated compound medium (B), but the Lewis acid catalyst do not migrate into the non-fluorinated compound medium (B). Further, the reaction product is sparingly soluble in the fluorinated compound medium (A) and, therefore, the desired reaction product can be recovered easily by continuously withdrawing the reaction-formed non-fluorinated compound medium (B) phase containing the reaction product from the phase separation zone.

When a continuous reaction is performed using a tubular reactor, the reactor may be equipped with a partition plate, wherein the surface of the partition plate is perpendicular to the flow direction of the reactor. The partition plate can be used for effectively performing the phase separation of the fluorinated compound medium (A) phase and the non-fluorinated compound medium (B) phase. Further, a reaction vessel equipped with an agitator can be used for increasing the reaction efficiency, and in this case, the reaction mixture can be continuously withdrawn from the upper portion of the reaction vessel and the withdrawn reaction mixture can be fed into a decanter to thereby perform the phase separation of the reaction mixture into a reaction-formed fluorinated compound medium (A) phase containing the Lewis acid catalyst and a reaction-formed non-fluorinated compound medium (B) phase containing the reaction product. The separated mobile phase (non-fluorinated compound medium (B) phase) containing the reaction product can be continuously withdrawn from the decanter and the separated stationary phase (fluorinated compound medium (A) phase) containing the Lewis acid catalyst can be recycled to the reaction vessel. In addition, a Lewis acid-catalyzed reaction can be performed in the following manner. Instead of using a fluorinated compound medium (A) phase containing the Lewis acid catalyst as a stationary phase, the fluorinated compound medium (A) containing the Lewis acid catalyst is fed to a tubular reactor (pipe reactor) or a microreactor (a reactor having a fluid pathway diameter of not more than 1,000 μm, preferably 500 μm) simultaneously with a non-fluorinated compound medium (B) containing a reactant (i.e., mobile phase) to thereby perform a reaction. After the reaction, the reaction mixture is separated into a reaction-formed fluorinated compound medium (A) phase containing the Lewis acid catalyst and a reaction-formed non-fluorinated compound medium (B) phase containing a reaction product, and the reaction-formed non-fluorinated compound medium (B) phase containing a reaction product is recovered, thereby obtaining the reaction product advantageously. When a microreactor is used as a reaction zone, the diffusion of the reactant, the Lewis acid catalyst and the reaction product occurs rapidly between the fluorinated compound medium (A) phase and the non-fluorinated compound medium (B) phase and, hence, the reaction rate becomes improved.

In the continuous reaction method of the present invention, the flow rate of the mobile phase can be selected based on the activity of the Lewis acid catalyst and the amount of the reactant or reactants contained in the mobile phase. Further, when unreacted reactant or reactants remain inside the reaction-formed mobile phase, the mobile phase separated from the stationary phase can be recycled to the reactor so as to perform the reaction by contacting the mobile phase again with the stationary phase.

There is no particular limitation with respect to the reaction which can be performed continuously by the method of the present invention as long as a compound represented by formula (1) or (2) above is capable of catalyzing the reaction. Examples of such reactions include a carbon-carbon bond-forming reaction, an oxidation reaction, a reduction reaction, a dehydration reaction, an esterification reaction and a transesterification reaction. Specifically, there can be mentioned the Diels-Alder reaction, the Michael reaction, the Friedel-Crafts reaction, a synthetic reaction of a Schiff base, the Fries rearrangement reaction, a methylolation reaction of a benzene nucleus, the Meerwein-Ponndorf-Verley reduction reaction, an aldol reaction, an esterification reaction, a transesterification reaction, the Mannich reaction, an oxidation reaction with hydrogen peroxide, an organic peroxide or molecular oxygen, a dehydration reaction of an alcohol, an O-glycosidation reaction, and a polymerization reaction of an olefin.

As exemplified above, in the present invention, the Lewis acid-catalyzed reaction can be performed continuously by using a reaction vessel or a tubular reactor.

Further, according to the present invention, there is provided a Lewis acid catalyst which can be advantageously used in the above-mentioned Lewis acid catalyst composition and the continuous reaction method. More specifically, according to the present invention, there is provided the following Lewis acid catalysts (i) to (v):

(i) A Lewis acid catalyst which is a compound represented by the following formula (1'):

$$[(R_f^1 SO_2)(R_f^2 SO_2)N]_n M \qquad (1')$$

wherein:
each of $R_f^1$ and $R_f^2$ independently represents a substituent selected from the group consisting of a perfluorinated, saturated $C_9$–$C_{16}$ hydrocarbon group containing in the skeleton thereof at least one heteroatom selected from the group consisting of a nitrogen atom and an oxygen atom and a partially substituted derivative thereof, wherein, in the partially substituted derivative in the definition of the substituent, a part of the fluorine atoms in the perfluorinated hydrocarbon group is replaced by at least one member selected from the group consisting of a hydrogen atom and a halogen atom exclusive of a fluorine atom, provided that, in the substituent, a part of the fluorine atoms bonded to the carbon atom directly bonded to the —$SO_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M;

(ii) A Lewis acid catalyst which is a compound represented by formula (1') above, wherein each of $R_f^1$ and $R_f^2$ in the formula (1') represents a substituent represented by the following formula (3):

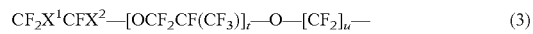

$$CF_2X^1 CFX^2-[OCF_2CF(CF_3)]_t-O-[CF_2]_u- \qquad (3)$$

wherein, each of $X^1$ and $X^2$ independently represents an atom selected from the group consisting of a halogen atom and a hydrogen atom; t is an integer of from 1 to 4; and u is an integer of from 1 to 4, preferably from 2 to 4, more preferably from 2 to 3;

(iii) A Lewis acid catalyst which is a compound represented by the following formula (2'):

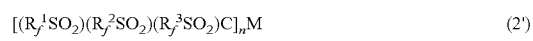

$$[(R_f^1 SO_2)(R_f^2 SO_2)(R_f^3 SO_2)C]_n M \qquad (2')$$

wherein:
each of $R_f^1$ to $R_f^3$ in the formula (2') represents a substituent represented by the following formula (3):

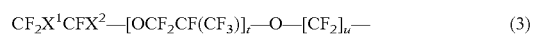

$$CF_2X^1 CFX^2-[OCF_2CF(CF_3)]_t-O-[CF_2]_u- \qquad (3)$$

wherein, each of $X^1$ and $X^2$ independently represents an atom selected from the group consisting of a halogen atom and a hydrogen atom; t is an integer of from 1 to 4; and u is an integer of from 1 to 4, preferably from 2 to 4, more preferably from 2 to 3;

M represents an atom selected from the group consisting of transition metals including rare earth metals, gallium, indium, thallium, silicon, germanium, tin, lead, antimony and bismuth; and n is an integer equivalent to the valence of M;

(iv) A Lewis acid catalyst which is at least one compound selected from the group consisting of compounds respectively represented by the following formulae (5) and (6):

and

wherein:
each of $R_f^1$ to $R_f^3$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent (β) selected from the group consisting of a perfluorinated, saturated or unsaturated $C_1$–$C_{16}$ hydrocarbon group containing no heteroatom and a partially substituted derivative thereof, provided that, in formula (5) above, at least one member selected from the group consisting of $R_f^1$ and $R_f^2$ is the substituent (α) and, in formula (6) above, at least one member selected from the group consisting of $R_f^1$ to $R_f^3$ is the substituent (α), wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —$SO_2$ group is not replaced by a hydrogen atom; and n is an integer equivalent to the valence of Sn; and (v) A Lewis acid catalyst which is at least one compound selected from the group consisting of compounds respectively represented by the following formulae (7) and (8):

and

wherein:
each of $R_f^1$ to $R_f^3$ independently represents a substituent (α) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent (β) selected from the group consisting of a perfluorinated, saturated or unsaturated $C_1$–$C_{16}$ hydrocarbon group containing no heteroatom and a partially substituted derivative thereof, provided that, in formula (7) above, at least one member selected from the group consisting of $R_f^1$ and $R_f^2$ is the substituent (α) and, in formula (8) above, at least one member selected from the group consisting of $R_f^1$ to $R_f^3$ is the substituent (α), wherein, in the partially substituted derivative in the definition of each of the substituents (α) and (β), a part of the fluorine atoms in the perfluorinated hydrocarbon group is replaced by at least one member selected from the group consisting of a hydrogen atom and a halogen atom exclusive of a fluorine atom, provided that, in each of the substituents (α) and (β), a part of the fluorine atoms bonded to a carbon atom directly bonded to the —$SO_2$ group is not replaced by a hydrogen atom; and n is an integer equivalent to the valence of Hf.

The Lewis acid catalysts of the present invention are specific examples of compounds represented by formula (1) or (2) above. Therefore, the characteristics of substituents (α) and (β) and partially substituted derivative thereof are the same as those described in connection with the Lewis acid catalyst composition of the present invention, unless otherwise specified.

Further, the reactions which can be performed using the Lewis acid catalysts of the present invention and the reaction conditions for performing such reactions are also the same as those described in connection with the Lewis acid catalyst contained in the Lewis acid catalyst composition of the present invention and the continuous reaction method of the present invention.

When the Lewis acid catalyst is a compound selected from the group consisting of compounds respectively represented by formula (1), (2), (1') and (2'), wherein M in the formula represents tin (Sn), the Lewis acid catalyst is advantageous for use in catalyzing an oxidation reaction of a ketone compound by use of hydrogen peroxide. Such Lewis acid catalyst has high catalytic activity and, even when the hydrogen peroxide concentration of the reaction system is as low as 10 to 30% by weight, based on the weight of the reaction system, the Lewis acid catalyst maintains its high catalytic activity and enables the reaction to proceed with high selectivity. Specific examples of ketone compounds used as a raw material for a Lewis acid-catalyzed reaction include saturated or unsaturated aliphatic ketones having a linear or a branched configuration, alicyclic ketones and aromatic ketones. Specific examples of aliphatic ketones include those having 3 to 30 carbon atoms, such as acetone, methyl ethyl ketone, diethyl ketone, dipropyl ketone, dibutyl ketone, dipentyl ketone, dihexyl ketone and dioctyl ketone. Specific examples of alicyclic ketones include those having 5 to 20 carbon atoms, such as cyclopentanone, cyclohexanone, cycloheptanone and cyclooctanone. Specific examples of aromatic ketones include those having 6 to 20 carbon atoms, such as acetophenone, propiophenone, butyrophenone, pentanophenone, heptanophenone, octanophenone and nonanophenone. A conventional hydrogen peroxide solution, namely a 10 to 60% by weight aqueous hydrogen peroxide can be used as an oxidizing agent, but from the viewpoint of safety, it is preferred to use a 30 to 40% by weight aqueous hydrogen peroxide. The molar ratio of hydrogen peroxide to a ketone compound is from 0.1 to 2, preferably from 0.3 to 1.5, more preferably from 0.5 to 1.2.

When a Lewis acid catalyst is a compound selected from the group consisting of compounds respectively represented by formula (1), (2), (1') and (2'), wherein M in the formula represents tin, the Lewis acid catalyst exhibits high catalytic activity for catalyzing a transesterification reaction. Examples of ester compounds used as a raw material for a Lewis acid-catalyzed reaction include saturated or unsaturated $C_2$–$C_{30}$ aliphatic esters having a linear or a branched configuration, alicyclic esters and aromatic esters. Examples of alcohols used as a raw material for a Lewis acid-catalyzed reaction include saturated or unsaturated $C_1$–$C_{30}$ aliphatic alcohols having a linear or a branched configuration and alicyclic alcohols.

When a Lewis acid catalyst is a compound selected from the group consisting of compounds respectively represented by formula (1), (2), (1') and (2'), wherein M in the formula represents hafnium, the Lewis acid catalyst can be used for catalyzing a reaction selected from the group consisting of a carbon-carbon bond-forming reaction, a dehydration reaction and an oxidation reaction with hydrogen peroxide. Such a Lewis acid catalyst exhibits very high catalytic activity when it is used in carbon-carbon bond-forming reactions, such as the Diels-Alder reaction, the Michael reaction, the Friedel-Crafts reaction, the Fries rearrangement reaction, a methylolation reaction of a benzene nucleus, an aldol reaction, an esterification reaction by dehydration of an alcohol and a carboxylic acid, an etherification reaction by a dehydration reaction of an alcohol, an oxidation reaction with hydrogen peroxide, and a polymerization reaction of an olefin.

The advantages of phase separation are utilized in the above-mentioned continuous reaction method of the present invention. Alternatively, the Lewis acid catalyst of the present invention can be immobilized to an inorganic or macromolecular carrier to thereby obtain an immobilized catalyst. In a solid phase-liquid phase reaction, a continuous reaction can be performed easily by simply passing a mobile phase in a liquid form through a stationary phase in a solid form. For example, as described in Japanese Patent Application Laid-Open Specification Nos. Hei 11-322758 and 2000-264903, the Lewis acid catalyst of the present invention can be immobilized to cyclodextrin or derivative thereof to thereby obtain an immobilized catalyst, and such an immobilized catalyst can be used for performing a continuous reaction in the above-mentioned manner.

Hereinbelow, an explanation is made on a method for producing a Lewis acid catalyst used in the Lewis acid catalyst composition and the continuous reaction method of the present invention and the Lewis acid catalyst of the present invention.

With respect to the production of the Lewis acid catalyst used in the Lewis acid catalyst composition and the continuous reaction method of the present invention, which is a compound selected from the group consisting of compounds respectively represented by formula (1) and (2) above, and to the production of the Lewis acid catalysts (i) to (v) of the present invention, substantially the same method can be used. With respect to the ligands which are the starting materials for the Lewis acid catalyst, both a perfluorinated hydrocarbon group containing in the skeleton thereof a nitrogen atom and/or an oxygen atom and a partially substituted derivative thereof can be synthesized under conditions which are substantially the same as those for synthesizing a perfluorinated hydrocarbon group.

A method for synthesizing a metal salt of a so-called C10 imide is explained as an example of a method for synthesizing a compound represented by formula (1) above.

In the present specification, the term "C10 imide" means a compound represented by the following formula:

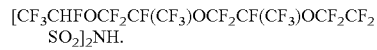

Firstly, $CF_3CF(COF)OCF_2CF(CF_3)OCF_2CF(CF_3)$ $OCF_2CF_2SO_2F$ is heated in the presence of sodium carbonate for performing a heat decarboxylation in water, to thereby obtain $CF_3CHFOCF_2CF(CF_3)OCF_2CF(CF_3)$ $OCF_2CF_2SO_2F$. Next, the obtained compound is reacted with a tetrahydrofuran solution of sodium bis(trimethylsilyl) amide at around room temperature and, then, the reaction mixture is condensed under reduced pressure to thereby obtain solid product 1. The obtained solid product 1 is reacted with $CF_3CHFOCF_2CF(CF_3)OCF_2CF(CF_3)OCF_2$ $CF_2SO_2F$ in the presence of dioxane (as a solvent) at 80° C. to 130° C. Subsequently, the reaction mixture is condensed under reduced pressure to thereby obtain solid product 2. The thus obtained solid product 2 is treated with either sulfuric acid or strongly acidic ion exchange resin, thereby obtaining a C10 imide.

Other imide compounds which are different in the number of carbon atoms can be synthesized under substantially the same conditions.

The C10 imide synthesized in the above-mentioned manner is reacted with a metal compound selected from the group consisting of a metal carbonate, a metal oxide, a metal hydroxide or a metal acetate at a temperature in the range of from room temperature to 100° C. in a solvent selected from the group consisting of water, an organic solvent and a mixture of water and an organic solvent. Subsequently, water and/or the organic solvent is removed from the resultant reaction mixture by heating or drying under reduced pressure to thereby obtain a metal salt of the C10 imide.

A method for synthesizing a metal salt of a so-called C10 methide is explained as an example of a method for synthesizing a compound represented by formula (2) above.

In the present specification, the term "C10 methide" means a compound represented by the following formula:

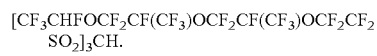

Synthesis of a C10 methide can be performed, for example, in accordance with the method described in U.S. Pat. No. 5,554,664. Specifically, $CF_3CHFOCF_2CF(CF_3)$— $OCF_2CF(CF_3)OCF_2CF_2SO_2F$ is added to a solution of methyl-magnesium chloride in tetrahydrofuran, thereby performing a reaction therebetween. Subsequently, the resultant reaction mixture is treated with sulfuric acid, followed by a treatment with cesium carbonate, to thereby isolate a reaction product (C10 methide) from the reaction mixture in the form of a cesium salt thereof. The thus obtained cesium salt of the C10 methide is treated with sulfuric acid to form a protonic acid, thereby obtaining the C10 methide.

For example, a method described in Unexamined Japanese Patent Application Publication No. 2000-219692 can be used to synthesize a rare earth metal salt of a C10 methide. In general, the C10 methide is reacted with a desired metal compound selected from the group consisting of a metal carbonate, a metal oxide, a metal hydroxide and a metal acetate at a temperature of from room temperature to 100° C. in a solvent selected from the group consisting of water, an organic solvent and a mixture of water and an organic solvent. Subsequently, water and/or the organic solvent are removed from the resultant reaction mixture by heating or drying under reduced pressure to thereby obtain a metal salt of the C10 methide.

BEST MODE FOR CARRYING OUT THE INVENTION

Hereinbelow, the present invention will be described in more detail with reference to the following Examples and Comparative Examples, which should not be construed as limiting the scope of the present invention.

EXAMPLE 1

<Synthesis of a Compound Represented by Formula (1)>

1) Synthesis of $CF_3CHFOCF_2CF(CF_3)OCF_2CF(CF_3)OCF_2CF_2SO_2F$ 500 g of $CF_3CF(COF)OCF_2CF(CF_3)OCF_2CF(CF_3)OCF_2CF_2SO_2F$ was dropwise added to a slurry containing 86.3 g of sodium carbonate and 500 ml of tetraethylene glycol dimethyl ether at 70° C. under a flow of nitrogen gas, followed by stirring at 70° C. for 2 hours, to thereby perform a reaction therebetween. 13 ml of water was added to the resultant reaction mixture, and the mixture was further stirred at 70° C. for 1 hour. Subsequently, the resultant mixture was heated at 160° C. for 2 hours to thereby perform a decarboxylation reaction. After the decarboxylation reaction, the decarboxylated reaction mixture was subjected to vacuum distillation (under a pressure of 2.7 kPa) and the generated vapor was condensed and recovered as a distillate. The distillate was washed with water, followed by drying. The dried distillate was further subjected to vacuum distillation (under a pressure of 2.7 kPa) and a distillate having a boiling point in the range of from 95 to 96° C. was recovered, thereby obtaining 184.71 g of a transparent liquid. The results of the $^{19}$F-NMR and $^1$H-NMR analyses of the obtained liquid are shown below:

$^{19}$F-NMR: δ (ppm, standard substance: $CFCl_3$, solvent: deuterated chloroform $(CDCl_3)$)=−148.3 (1F), −147.0 (1F), −146.6 (1F), −114.6 (2F), −88.4 (1F), −87.0 (3F), −85.9 (1F), −81.2 to −82.7 (10F) and 42.6 (1F); and $^1$H-NMR: δ (ppm, standard substance: $(CH_3)_4Si$, solvent: $CDCl_3$)=5.9.

From these results, the obtained liquid was confirmed to be $CF_3CHFOCF_2CF(CF_3)OCF_2CF(CF_3)OCF_2CF_2SO_2F$.

2) Synthesis of an Imide Compound

A 500 ml three-necked flask was purged with nitrogen gas and thereto was added 20.6 g of $CF_3CHFOCF_2CF—(CF_3)OCF_2CF(CF_3)OCF_2CF_2SO_2F$ synthesized in item 1) above, followed by stirring in an ice bath (10° C. or lower). Then, 21.6 ml of a tetrahydrofuran solution containing 0.0216 mol of sodium bis(trimethylsilyl)amide was dropwise added to the $CF_3CHFOCF_2CF(CF_3)OCF_2CF(CF_3)OCF_2CF_2SO_2F$ in the flask over 30 minutes to perform a reaction therebetween in two steps. Illustratively stated, a reaction between $CF_3CHFOCF_2CF(CF_3)OCF_2CF(CF_3)OCF_2CF_2SO_2F$ and sodium bis(trimethylsilyl)amide was first performed at 10° C. or lower for 3 hours and, then, performed at room temperature for 19 hours. The resultant reaction mixture was condensed under reduced pressure (133 to 4000 Pa) at 60° C., thereby obtaining a solid product. 15.6 g of the obtained solid product was added to a mixture of 50 ml of dioxane and 27.3 g of $CF_3CHFOCF_2CF—(CF_3)OCF_2CF(CF_3)OCF_2CF_2SO_2F$, and the resultant mixture was placed in an autoclave to perform a reaction therebetween at 120° C. for 13 hours.

After the reaction, the reaction mixture was condensed under a reduced pressure (133 Pa) at 60° C., thereby obtaining liquid substance (a). The obtained liquid substance (a) was added to 100 ml of 6 N hydrochloric acid, followed by stirring at room temperature for 1 hour. From the resultant was separated an oil phase, and the separated oil phase was washed with water and extracted with 50 ml of isopropyl ether. The residual isopropyl ether was distilled off from the oil phase under a reduced pressure (1330 Pa) at 50° C., thereby obtaining 14 g of liquid substance (b). The thus obtained liquid substance (b) was further subjected to distillation at a temperature of from 120 to 160° C. under a reduced pressure (2.7 Pa), thereby obtaining 7.3 g of a liquid product. The results of the $^{19}$F-NMR and $^1$H-NMR analyses of the obtained liquid product are shown below:

$^{19}$F-NMR: δ (ppm, standard substance: $CF_3C_6H_5$, solvent: $CDCl_3$)=−148.3 (2F), −148.0 to −147.0 (2F), −147.0 to −146.0 (2F), −113.7 (4F), −89.0 to −88.0 (2F), −86.9 (6F), −86.0 to −85.0 (2F), −82.4 (6F), −82.2 (6F), −83.0 to −82.0 (2F), −81.6 (2F), −79.8 (2F) and −79.2 (2F); and $^1$H-NMR: δ (ppm, standard substance: $(CH_3)_4Si$, solvent: $CDCl_3$)=5.87 (2H) and 7.84 (1H).

From these results, the above-mentioned liquid product was confirmed to be a so-called C10 imide which is a compound represented by the following formula:

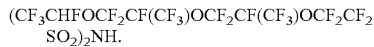

Further, a so-called C10,8 imide and a so-called C10*,10 imide, which are compounds represented by the following formulae, were individually synthesized in substantially the same manner as mentioned above, except that starting materials corresponding to the above-mentioned compounds are used:

C10,8 imide:

C10*,10 imide:
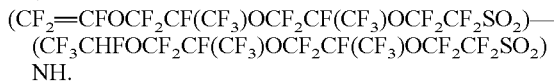

3) Synthesis of a Metal Salt 5 g of the C10 imide synthesized in item 2) above was dissolved in a mixed solvent of 10 ml of water and 15 ml of acetonitrile, followed by addition of 0.45 g of ytterbium carbonate, to perform a reaction therebetween in two steps. Illustratively stated, a reaction between the C10 imide and ytterbium carbonate was first performed at 20° C. for 5 hours and, then, performed at 50° C. for 1 hour. The resultant reaction mixture was filtered at room temperature to remove a precipitate contained therein, thereby obtaining a filtrate. The obtained filtrate was evaporated to dryness by vacuum condensation at 50° C. under a pressure of from 133 to 1330 Pa and, then, dried at 90° C. under a pressure of 1.3 Pa for 24 hours, thereby obtaining 4.7 g of a ytterbium salt of the C10 imide (hereinafter, referred to as "ytterbium tris[bis (C10)imide]") as white solids.

The results of the elementary analysis of the obtained ytterbium salt of the C10 imide are shown below (theoretical values are shown in parentheses):

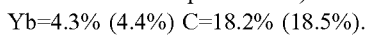

Further, other metal salts of the C10 imide were synthesized as follows.

A scandium salt of the C10 imide (hereinafter, referred to as "scandium tris[bis(C10)imide]") was synthesized in substantially the same manner as mentioned above, except that scandium acetate was used instead of ytterbium carbonate.

A lanthanum salt and an yttrium salt of the C10 imide were individually synthesized in substantially the same manner as mentioned above, except that lanthanum carbonate and yttrium carbonate were, respectively, used instead of ytterbium carbonate.

A tin salt and a hafnium salt of the C10 imide were individually synthesized in substantially the same manner as mentioned above, except that tin(IV) acetate and hafnium chloride were individually reacted with the C10 imide in the presence of acetonitrile (as a solvent) at 60° C. for 15 hours.

In addition, metal salts of the C10*,10 imide and metal salts of the C10,8 imide were synthesized in substantially the same manner as mentioned above by using appropriate metal compounds. The results of the elementary analysis of the representative examples of the metal salts of the C10 imide, C10*,10 imide and C10,8 imide are shown below (theoretical values are shown in parentheses):

(1) Scandium tris[bis(C10)imide]
    Sc=1.1% (1.2%) C=18.9% (19.1%),
(2) Lanthanum tris[bis(C10*,10)imide]
    La=3.6% (3.7%) C=18.8% (19.0%), and
(3) Ytterbium tris[bis(C10,8)imide]
    Yb=4.7% (4.9%) C=18.6% (18.5%).

EXAMPLE 2

<Synthesis of a Compound Represented by Formula (2)>

5.0 g of a so-called C10 methide represented by the following formula:

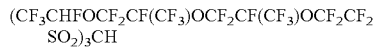
$(CF_3CHFOCF_2CF(CF_3)OCF_2CF(CF_3)OCF_2CF_2SO_2)_3CH$ was dissolved in a mixed solvent of 10 ml of water and 10 ml of acetonitrile, followed by addition of 0.20 g of scandium acetate, to perform a reaction therebetween in two steps. Illustratively stated, a reaction between the C10 methide and scandium acetate was first performed at 20° C. for 5 hours and, then, performed at 50° C. for 1 hour. The resultant reaction mixture was evaporated to dryness by vacuum condensation at 50° C. under a pressure of from 133 to 1330 Pa and, then, dried at 90° C. under a pressure of 1.3 Pa for 24 hours, thereby obtaining 4.5 g of a scandium salt of the C10 methide (hereinafter, referred to as "scandium tris[tris(C10)methide]") as white solids.

The results of the elementary analysis of the obtained scandium salt of the C10 methide are shown below (theoretical values are shown in parentheses):
    Sc=0.8% (0.8%) C=20.0% (19.9%).

A ytterbium salt of the C10 methide (hereinafter, referred to as "ytterbium tris[tris(C10)methide]") was synthesized in substantially the same manner as mentioned above, except that ytterbium carbonate was used instead of scandium acetate. The results of the elementary analysis of the obtained ytterbium tris[tris(C10)methide] are shown below (theoretical values are shown in parentheses):
    Yb=2.9% (3.0%) C=19.3% (19.5%).

Further, other metal salts of the C10 methide were synthesized as follows.

A lanthanum salt of the C10 methide was synthesized in substantially the same manner as mentioned above, except that lanthanum carbonate was used instead of ytterbium carbonate.

A tin salt and a hafnium salt of the C10 methide were individually synthesized in substantially the same manner as mentioned above, except that tin(IV) acetate and hafnium chloride were individually reacted with the C10 methide in the presence of acetonitrile (as a solvent) at 60° C. for 15 hours.

In addition, other metal salts of the C10 methide were synthesized in substantially the same manner as mentioned above by using appropriate metal compounds.

EXAMPLE 3

As a Lewis acid catalyst, ytterbium tris[bis(C10)imide] was added to a mixed medium of 4 ml of perfluoromethylcyclohexane and 4 ml of dichloroethane, thereby obtaining a Lewis acid catalyst composition. The amount of Lewis acid catalyst added was adjusted so that it would be 3 mol %, based on the molar amount of 2,3-dimethylbutadiene to be added to the Lewis acid catalyst composition. To the obtained Lewis acid catalyst composition were added 224 μl of 2,3-dimethylbutadiene and 248 μl of methyl vinyl ketone to obtain a mixture. Then, the mixture was stirred to thereby perform a reaction between the 2,3-dimethylbutadiene and the methyl vinyl ketone at 30° C. for 10 hours. Then, the stirred reaction mixture was allowed to stand still at room temperature, wherein the reaction mixture rapidly separated into two phases within 10 seconds. The time needed for this phase separation (i.e., time needed for the stirred reaction mixture to separate into two phases as in the case of the mixture prior to the stirring to perform the reaction) was determined by visually observing the reaction mixture and measuring with a stopwatch the time from the discontinuation of the stirring of the reaction mixture to the formation of the two phases in the reaction mixture.

The reaction mixture was analyzed by gas chromatography (GC-1700 AF type gas chromatograph; manufactured and sold by Shimadzu Corporation, Japan). It was found that the overall yield of the reaction product (i.e., 4-acetyl-1,2-dimethylcyclohexene) in the upper and lower phases was 94%, wherein 98% of the produced 4-acetyl-1,2-dimethylcyclohexene was present in the lower phase. Subsequently, the amounts of ytterbium tris-[bis(C10)imide] present in the upper phase and the lower phase were individually measured in terms of the amounts of ytterbium by plasma emission spectrometry (IRIS/AP type plasma emission spectrometry apparatus; manufactured and sold by Nippon Jarrell Ash, Japan). It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dichloroethane and perfluoromethylcyclohexane, respectively, so that separation therebetween can be performed easily.

Comparative Example 1

A reaction was performed in substantially the same manner as in Example 3, except that ytterbium tris[bis(perfluorooctanesulfonyl)imide] was used as the Lewis acid catalyst. As a result, it was found that the overall yield of the reaction product (i.e., 5-acetyl-2,3-dimethyl-cyclohexa-2-ene) in the upper and lower phases was only 84%. When the reaction mixture was allowed to stand still at room temperature, the phase separation of the reaction mixture into two phases took about 40 seconds. The amounts of ytterbium tris[bis(perfluorooctanesulfonyl)imide] present in the upper phase and the lower phase were individually measured in terms of the amounts of ytterbium by plasma emission spectrometry.

As a result, it was found that 99.3% of the Lewis acid catalyst was present in the lower phase.

EXAMPLE 4

224 μl of 2,3-dimethylbutadiene and 248 μl of methyl vinyl ketone were added to a mixed medium of 3 ml of perfluoromethylcyclohexane and 3 ml of dichloromethane. To the resultant mixture was added 2 mol % of scandium tris[bis(C10)imide] (as a Lewis acid catalyst), based on the molar amount of the 2,3-dimethylbutadiene, thereby obtaining a Lewis acid catalyst composition containing the 2,3-dimethylbutadiene and the methyl vinyl ketone. Then, the obtained Lewis acid catalyst composition containing the 2,3-dimethylbutadiene and the methyl vinyl ketone was stirred to thereby perform a reaction between the 2,3-dimethylbutadiene and the methyl vinyl ketone at 30° C. for 8 hours. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., 4-acetyl-1,2-dimethylcyclohexene) in the upper and lower phases was 95%, wherein 99% of the produced 4-acetyl-1,2-dimethylcyclohexene was present in the upper phase and 1% of the produced 4-acetyl-1,2-dimethylcyclohexene was present in the lower phase. Subsequently, the amounts of scandium tris[bis(C10)imide] present in the upper phase and the lower phase were individually measured in terms of the amounts of scandium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dichloromethane and perfluoromethylcyclohexane, respectively, so that separation therebetween can be performed easily.

Comparative Example 2

A reaction was performed in substantially the same manner as in Example 4, except that scandium tris[bis(perfluorooctanesulfonyl)imide] was used as the Lewis acid catalyst. As a result, it was found that the overall yield of the reaction product (i.e., 4-acetyl-1,2-dimethylcyclohexene) in the upper and lower phases was only 82%. When the reaction mixture was allowed to stand still at room temperature, the phase separation of the reaction mixture into two phases took about 40 seconds. The amounts of scandium tris[bis (perfluorooctanesulfonyl)imide] present in the upper phase and the lower phase were individually measured in terms of the amounts of scandium by plasma emission spectrometry. As a result, it was found that 99.3% of the Lewis acid catalyst was present in the lower phase.

EXAMPLE 5

224 μl of 2,3-dimethylbutadiene and 248 μl of methyl vinyl ketone were added to a mixed medium of 4 ml of perfluorooctane and 5 ml of dioxane. To the resultant mixture was added 5 mol % of lanthanum tris-[bis(C10*,10) imide] (as a Lewis acid catalyst), based on the molar amount of the 2,3-dimethylbutadiene, thereby obtaining a Lewis acid catalyst composition containing the 2,3-dimethylbutadiene and the methyl vinyl ketone. The obtained Lewis acid catalyst composition containing the 2,3-dimethylbutadiene and the methyl vinyl ketone was stirred to thereby perform a reaction between the 2,3-dimethylbutadiene and the methyl vinyl ketone at 30° C. for 11 hours. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., 4-acetyl-1,2-dimethylcyclohexene) in the upper and lower phases was 93%, wherein 99% of the produced 4-acetyl-1,2-dimethylcyclohexene was present in the upper phase and 1% of the produced 4-acetyl-1,2-dimethylcyclohexene was present in the lower phase. Subsequently, the amounts of lanthanum tris[bis(C10,10) imide] present in the upper phase and the lower phase were individually measured in terms of the amounts of lanthanum by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dioxane and perfluorooctane, respectively, so that separation therebetween can be performed easily.

EXAMPLE 6

216 mg of anisole and 410 mg of acetic anhydride were added to a mixed medium of 4 ml of perfluoromethylcyclohexane and 5 ml of chlorobenzene. To the resultant mixture was added 10 mol % of ytterbium tris[bis(C10)imide] (as a Lewis acid catalyst), based on the molar amount of the anisole, thereby obtaining a Lewis acid catalyst composition containing the anisole and the acetic anhydride. The obtained Lewis acid catalyst composition containing the anisole and the acetic anhydride was stirred to thereby perform a reaction between the anisole and the acetic anhydride at 70° C. for 8 hours. Then, the stirred reaction mixture was cooled to room temperature and the cooled reaction mixture was allowed to stand still at room temperature, wherein the reaction mixture rapidly separated into two phases within 10 seconds.

The reaction mixture was analyzed by gas chromatography. It was found that the overall yield of the reaction product (i.e., p-methoxyacetophenone) in the upper and lower phases was 93%, wherein 98% of the produced p-methoxyacetophenone was present in the upper phase and 2% of the produced p-methoxyacetophenone was present in the lower phase. Subsequently, the amounts of ytterbium tris[bis(C10)imide] present in the upper phase and the lower phase were individually measured in terms of the amounts of ytterbium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in chlorobenzene and perfluoromethylcyclohexane, respectively, so that separation therebetween can be performed easily.

Comparative Example 3

A reaction was performed in substantially the same manner as in Example 6, except that ytterbium tris[bis(perfluorooctanesulfonyl)imide] was used as the Lewis acid catalyst.

As a result, it was found that the overall yield of the reaction product (i.e., p-methoxyacetophenone) in the upper and lower phases was only 79%. When the reaction mixture was allowed to stand still at room temperature, the phase separation of the reaction mixture into two phases took about 45 seconds. The amounts of ytterbium tris[bis(perfluorooctanesulfonyl)imide] present in the upper phase and the lower phase were individually measured in terms of the amounts of ytterbium by plasma emission spectrometry. As a result, it was found that 99.1% of the Lewis acid catalyst was present in the lower phase.

EXAMPLE 7

216 mg of anisole and 410 mg of acetic anhydride were added to a mixed medium of 5 ml of perfluoromethylcyclohexane and 5 ml of chlorobenzene. To the resultant mixture was added 6 mol % of scandium tris[bis(C10)imide] (as a Lewis acid catalyst), based on the molar amount of the anisole, thereby obtaining a Lewis acid catalyst composition containing the anisole and the acetic anhydride. The obtained Lewis acid catalyst composition containing the anisole and the acetic anhydride was stirred to thereby perform a reaction between the anisole and the acetic anhydride at 70° C. for 5 hours. Then, the resultant reaction mixture was cooled to room temperature and the cooled reaction mixture was allowed to stand still at room temperature, wherein the reaction mixture rapidly separated into two phases within 10 seconds.

The reaction mixture was analyzed by gas chromatography. It was found that the overall yield of the reaction product (i.e., p-methoxyacetophenone) in the upper and lower phases was 90%, wherein 98% of the produced p-methoxyacetophenone was present in the upper phase and 2% of the produced p-methoxyacetophenone was present in the lower phase. Subsequently, the amounts of scandium tris[bis(C10)imide] present in the upper phase and the lower phase were individually measured in terms of the amounts of scandium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in chlorobenzene and perfluoromethylcyclohexane, respectively, so that separation therebetween can be performed easily.

Comparative Example 4

A reaction was performed in substantially the same manner as in Example 7, except that scandium tris[bis(perfluorooctanesulfonyl)imide] was used as the Lewis acid catalyst. As a result, it was found that the overall yield of the reaction product (i.e., p-methoxyacetophenone) in the upper and lower phases was only 74%. When the reaction mixture was allowed to stand still at room temperature, the phase separation of the reaction mixture into two phases took about 45 seconds. The amounts of scandium tris[bis(perfluorooctanesulfonyl)imide] present in the upper phase and the lower phase were individually measured in terms of the amounts of scandium by plasma emission spectrometry. As a result, it was found that 99.1% of the Lewis acid catalyst was present in the lower phase.

EXAMPLE 8

204 mg of cyclohexanol and 232 mg of acetic anhydride were added to a mixed medium of 4 ml of perfluorodecalin and 5 ml of toluene. To the resultant mixture was added 1 mol % of yttrium tris[bis(C10)imide] (as a Lewis acid catalyst), based on the molar amount of the cyclohexanol, thereby obtaining a Lewis acid catalyst composition containing the cyclohexanol and the acetic anhydride. The obtained Lewis acid catalyst composition containing the cyclohexanol and the acetic anhydride was stirred to thereby perform a reaction between the cyclohexanol and the acetic anhydride at 25° C. for 20 minutes. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., cyclohexyl acetate) in the upper and lower phases was 99%, wherein 99% of the produced cyclohexyl acetate was present in the upper phase and 1% of the produced cyclohexyl acetate was present in the lower phase. Subsequently, the amounts of yttrium tris[bis(C10)imide) present in the upper phase and the lower phase were individually measured in terms of the amounts of yttrium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in toluene and perfluorodecalin, respectively, so that separation therebetween can be performed easily.

Next, reactions were performed in substantially the same manner as mentioned above, except that the metal salts of the C10 imide shown in Table 1 below were individually used as a Lewis acid catalyst. The results are also shown in Table 1 below.

TABLE 1

| Metal species of the metal salts of the C10 imide | Yield of cyclohexyl acetate (%) |
| --- | --- |
| hafnium | 99 |
| tin(IV) | 94 |
| lead | 41 |
| cadmium | 53 |
| zinc | 51 |
| silver | 42 |
| bismuth | 79 |

Comparative Example 5

A reaction was performed in substantially the same manner as in Example 8, except that yttrium tris[bis(perfluorooctanesulfonyl)imide] was used as the Lewis acid catalyst. As a result, it was found that the overall yield of the reaction product (i.e., cyclohexyl acetate) in the upper and lower phases was only 94%. When the reaction mixture was allowed to stand still at room temperature, the phase separation of the reaction mixture into two phases took about 40 seconds. The amounts of yttrium tris[bis(perfluorooctanesulfonyl)imide] present in the upper phase and the lower phase were individually measured in terms of the amounts of yttrium by plasma emission spectrometry. As a result, it was found that 99.2% of the Lewis acid catalyst was present in the lower phase.

EXAMPLE 9

81 mg of benzaldehyde and 165 mg of dimethylketene methyl trimethylsily acetal were added to a mixed medium of 5 ml of perfluorooctane and 4 ml of toluene. To the resultant mixture was added 1 mol % of ytterbium tris[tris (C10)methide] (as a Lewis acid catalyst), based on the molar amount of the benzaldehyde, thereby obtaining a Lewis acid catalyst composition containing the benzaldehyde and the dimethylketene methyl trimethylsilyl acetal. The obtained Lewis acid catalyst composition containing the benzaldehyde and the dimethylketene methyl trimethylsily acetal was stirred to thereby perform a reaction between the benzaldehyde and the dimethylketene methyl trimethylsily acetal at 25° C. for 10 minutes. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., methyl 3-trimethylsilyloxy-2,2-dimethyl-3-phenylpropionate) in the upper and lower phases was 88%, wherein 99% of the produced methyl 3-trimethylsilyloxy-2,2-dimethyl-3-phenylpropionate was present in the upper phase and 1% of the produced methyl 3-trimethylsilyloxy-2,2-dimethyl-3-phenylpropionate was present in the lower phase. Subsequently, the amounts of ytterbium tris(tris(C10) methide] present in the upper phase and the lower phase were individually measured in terms of the amounts of ytterbium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in toluene and perfluorooctane, respectively, so that separation therebetween can be performed easily.

Comparative Example 6

A reaction was performed in substantially the same manner as in Example 9, except that ytterbium tris-[tris(perfluorooctanesulfonyl)methide] was used as the Lewis acid catalyst. As a result, it was found that the overall yield of the reaction product (i.e., methyl 3-trimethylsilyloxy-2,2-dimethyl-3-phenylpropionate) in the upper and lower phases was only 74%. When the reaction mixture was allowed to stand still at room temperature, the phase separation of the reaction mixture into two phases took about 40 seconds. The amounts of ytterbium tris[bis(perfluorooctanesulfonyl)methide] present in the upper phase and the lower phase were individually measured in terms of the amounts of ytterbium by plasma emission spectrometry. As a result, it was found that 99.3% of the Lewis acid catalyst was present in the lower phase.

EXAMPLE 10

81 mg of benzaldehyde and 165 mg of methyl dimethylketene trimethylsilyl acetal were added to a mixed medium of 2 ml of perfluorodecalin and 4 ml of dichloroethane. To the resultant mixture was added 0.5 mol % of scandium tris[tris(C10)methide] (as a Lewis acid catalyst), based on the molar amount of the benzaldehyde, thereby obtaining a Lewis acid catalyst composition containing the benzaldehyde and the dimethylketene methyl trimethylsily acetal. The obtained Lewis acid catalyst composition containing the benzaldehyde and the dimethylketene methyl trimethylsilyl acetal was stirred to thereby perform a reaction between the benzaldehyde and the dimethylketene methyl trimethylsily acetal at 25° C. for 10 minutes. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., methyl 3-trimethylsilyloxy-2,2-dimethyl-3-phenylpropionate) in the upper and lower phases was 86%, wherein 99% of the produced methyl 3-trimethylsilyloxy-2,2-dimethyl-3-phenylpropionate was present in the upper phase and 1% of the produced methyl 3-trimethylsilyloxy-2,2-dimethyl-3-phenylpropionate was present in the lower phase. Subsequently, the amounts of scandium tris[tris(C10) methide] present in the upper phase and the lower phase were individually measured in terms of the amounts of scandium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dichloroethane and perfluorodecalin, respectively, so that separation therebetween can be performed easily.

Next, reactions were performed in substantially the same manner as mentioned above, except that the metal salts of the C10 methide shown in Table 2 below were individually used as a Lewis acid catalyst. The results are also shown in Table 2 below.

TABLE 2

| Metal species of the metal salts of the C10 methide | Yield of methyl 3-tri-methylsilyloxy-2,2-dimethyl-3-phenyl-propionate (%) |
|---|---|
| hafnium | 93 |
| tin(IV) | 79 |
| lead | 51 |
| cadmium | 46 |
| gallium | 72 |

EXAMPLE 11

81 mg of benzaldehyde and 165 mg of dimethylketene methyl trimethylsilyl acetal were added to a mixed medium of 4 ml of perfluorohexane and 4 ml of dioxane. To the resultant mixture was added 1 mol % of lanthanum tris[tris (C10)methide] (as a Lewis acid catalyst), based on the molar amount of the benzaldehyde, thereby obtaining a Lewis acid catalyst composition containing the benzaldehyde and the dimethylketene methyl trimethylsily acetal. The obtained Lewis acid catalyst composition containing the benzaldehyde and the dimethylketene methyl trimethylsilyl acetal was stirred to thereby perform a reaction between the benzaldehyde and the dimethylketene methyl trimethylsily acetal at 25° C. for 10 minutes. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., methyl 3-trimethylsilyloxy-2,2-dimethyl-3-phenylpropionate) in the upper and lower phases was 81%, wherein 99% of the produced methyl 3-trimethylsilyloxy-2,2-dimethyl-3-phenylpropionate was present in the upper phase and 1% of the produced methyl 3-trimethylsilyloxy-2,2-dimethyl-3-phenylpropionate was present in the lower phase. Subsequently, the amounts of lanthanum tris[tris(C10)methide] present in the upper phase and the lower phase were individually measured in terms of the amounts of lanthanum by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dioxane and perfluorohexane, respectively, so that separation therebetween can be performed easily.

EXAMPLE 12

As a Lewis acid catalyst, ytterbium tris[bis(C10)imide] was added to a mixed medium of 4 ml of perfluorodecalin and 4 ml of dichloromethane, thereby obtaining a Lewis acid catalyst composition. The amount of Lewis acid catalyst added was adjusted so that it would be 1 mol %, based on the molar amount of benzaldehyde to be added to the Lewis acid catalyst composition. To the obtained Lewis acid catalyst composition were added 81 mg of benzaldehyde and 165 mg of dimethylketene methyl trimethylsily acetal to obtain a mixture. Then, the mixture was stirred to thereby perform a reaction between the benzaldehyde and the dimethylketene methyl trimethylsily acetal at 25° C. for 10 minutes. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., methyl 3-trimethylsilyloxy-2,2-dimethyl-3-phenylpropionate) in the upper and lower phases was 86%, wherein 99% of the produced methyl 3-trimethylsilyloxy-2,2-dimethyl-3-phenylpropionate was present in the upper phase and 1% of the produced methyl 3-trimethylsilyloxy-2,2-dimethyl-3-phenylpropionate was present in the lower phase. Subsequently, the amounts of ytterbium tris[bis(C10)imide] present in the upper phase and the lower phase were individually measured in terms of the amounts of ytterbium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in dichloromethane and perfluorodecalin, respectively, so that separation therebetween can be performed easily.

Comparative Example 7

A reaction was performed in substantially the same manner as in Example 12, except that ytterbium tris-[bis(perfluorooctanesulfonyl)imide] was used as the Lewis acid catalyst. As a result, it was found that the overall yield of the reaction product (i.e., methyl 3-trimethylsilyloxy-2,2-dimethyl-3-phenylpropionate) in the upper and lower phases was only 74%. When the reaction mixture was allowed to stand still at room temperature, the phase separation of the reaction mixture into two phases took about 40 seconds. The amounts of ytterbium tris[bis(perfluorooctanesulfonyl)imide] present in the upper phase and the lower phase were individually measured in terms of the amounts of ytterbium by plasma emission spectrometry. As a result, it was found that 99.3% of the Lewis acid catalyst was present in the lower phase.

EXAMPLE 13

216 mg of anisole and 410 mg of acetic anhydride were added to a mixed medium of 4 ml of perfluoromethylcyclohexane and 7 ml of chlorobenzene. To the resultant mixture was added 10 mol % of ytterbium tris[bis(C10)imide] (as a Lewis acid catalyst), based on the molar amount of the anisole, thereby obtaining a Lewis acid catalyst composition containing the anisole and the acetic anhydride. The obtained Lewis acid catalyst composition containing the anisole and the acetic anhydride was stirred to thereby perform a reaction between the anisole and the acetic anhydride at 70° C. for 8 hours. Then, the stirred reaction mixture was cooled to room temperature and the cooled reaction mixture was allowed to stand still at room temperature, wherein the reaction mixture rapidly separated into two phases (upper chlorobenzene phase and lower perfluoromethylcyclohexane) within 10 seconds.

The reaction mixture was analyzed by gas chromatography. It was found that the overall yield of the reaction product (i.e., p-methoxyacetophenone) in the upper and lower phases was 93%. Subsequently, the upper chlorobenzene phase containing the product was removed from the reaction mixture and, then, 7 ml of chlorobenzene, 216 mg of anisole and 410 mg of acetic anhydride were added to the remainder of the reaction mixture (i.e., perfluoromethylcyclohexane containing the catalyst) to obtain a mixture. Then, the mixture was stirred to thereby perform a reaction at 70° C. for 8 hours. Then, the stirred reaction mixture was allowed to stand still at room temperature, so that the reaction mixture separated into an upper phase and a lower phase. The reaction mixture was analyzed by gas chromatography. It was found that the overall yield of the reaction product (i.e., p-methoxyacetophenone) in the upper and lower phases was 92%. Substantially the same procedure as mentioned above was repeated further twice. The yields of p-methoxyacetophenone in the twice-repeated reactions were 94% and 93%, respectively.

EXAMPLE 14

204 mg of cyclohexanol and 232 mg of acetic anhydride were added to a mixed medium of 4 ml of perfluoromethylcyclohexane and 4 ml of toluene. To the resultant mixture was added 1 mol % of ytterbium tris[bis(C10)imide] (as a Lewis acid catalyst), based on the molar amount of the cyclohexanol, thereby obtaining a Lewis acid catalyst composition containing the cyclohexanol and the acetic anhydride. The obtained Lewis acid catalyst composition containing the cyclohexanol and the acetic anhydride was stirred to thereby perform a reaction between the cyclohexanol and the acetic anhydride at 30° C. for 15 minutes. Then, the stirred reaction mixture was allowed to stand still at room temperature, wherein the reaction mixture rapidly separated into two phases (upper toluene phase and lower perfluoromethylcyclohexane phase) within 10 seconds.

The reaction mixture was analyzed by gas chromatography. It was found that the overall yield of the reaction product (i.e., cyclohexyl acetate) in the upper and lower phases was 99%. Subsequently, the upper toluene phase containing the product was removed from the reaction mixture and, then, 4 ml of toluene, 204 mg of cyclohexanol and 232 mg of acetic anhydride were added to the remainder of the reaction mixture (i.e., perfluoromethylcyclohexane containing the catalyst) to obtain a mixture. Then, the mixture was stirred to thereby perform a reaction at 30° C. for 15 minutes. Then, the stirred reaction mixture was allowed to stand still at room temperature, so that the reaction mixture separated into an upper phase and a lower phase. The reaction mixture was analyzed by gas chromatography. It was found that the overall yield of the reaction product (i.e., cyclohexyl acetate) in the upper and lower phases was 99%. Substantially the same procedure as mentioned above was repeated further four times. The yields of the produced cyclohexyl acetate in the four times-repeated reactions were 99%, 100%, 99% and 100%, respectively.

EXAMPLE 15

224 µl of 2,3-dimethylbutadiene and 248 µl of methyl vinyl ketone were added to a mixed medium of 4 ml of perfluoromethylcyclohexane and 4 ml of cyclohexane. To the resultant mixture was added 3 mol % of ytterbium tris[bis(C10*,10)imide] (as a Lewis acid catalyst), based on the molar amount of the 2,3-dimethylbutadiene, thereby obtaining a Lewis acid catalyst composition containing the 2,3-dimethylbutadiene and the methyl vinyl ketone. The obtained Lewis acid catalyst composition containing the 2,3-dimethylbutadiene and the methyl vinyl ketone was stirred to thereby perform a reaction between the 2,3-dimethylbutadiene and the methyl vinyl ketone at 30° C. for 12 hours. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., 4-acetyl-1,2-dimethylcyclohexene) in the upper and lower phases was 94%, wherein 98% of the produced 4-acetyl-1,2-dimethylcyclohexene was present in the upper phase and 2% of the produced 4-acetyl-1,2-dimethylcyclohexene was present in the lower phase. Subsequently, the amounts of ytterbium tris[bis(C10*,10)imide] present in the upper phase and the lower phase were individually measured in terms of the amounts of ytterbium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in cyclohexane and perfluoromethyl cyclohexane, respectively, so that separation therebetween can be performed easily.

EXAMPLE 16

224 µl of 2,3-dimethylbutadiene and 248 µl of methyl vinyl ketone were added to a mixed medium of 3 ml of perfluoromethylcyclohexane and 3 ml of n-decane. To the resultant mixture was added 4 mol % of ytterbium tris[bis(C10,8)imide] (as a Lewis acid catalyst), based on the molar amount of the 2,3-dimethylbutadiene, thereby obtaining a Lewis acid catalyst composition containing the 2,3-dimethylbutadiene and the methyl vinyl ketone. The obtained Lewis acid catalyst composition containing the 2,3-dimethylbutadiene and the methyl vinyl ketone was stirred to thereby perform a reaction between the 2,3-dimethylbutadiene and the methyl vinyl ketone at 30° C. for 12 hours. Then, the stirred reaction mixture was allowed to stand still at room temperature, wherein the reaction mixture rapidly separated into two phases within 10 seconds.

The reaction mixture was analyzed by gas chromatography. It was found that the overall yield of the reaction product (i.e., 4-acetyl-1,2-dimethylcyclohexene) in the upper and lower phases was 92%, wherein 99% of the produced 4-acetyl-1,2-dimethylcyclohexene was present in the upper phase and 1% of the produced 4-acetyl-1,2-dimethylcyclohexene was present in the lower phase. Subsequently, the amounts of ytterbium tris[bis(C10,8)imide] present in the upper phase and the lower phase were individually measured in terms of the amounts of ytterbium by plasma emission spectrometry. It was found that not less than 99.9% of the Lewis acid catalyst was present in the lower phase.

Thus, it was confirmed that when the reaction is performed using the Lewis acid catalyst composition of the present invention, the product and the catalyst are separately dissolved in n-decane and perfluoromethylcyclohexane, respectively, so that separation therebetween can be performed easily.

EXAMPLE 17

216 mg of anisole and 480 mg of acetic anhydride were added to a mixed medium of 6 ml of perfluoromethylcyclohexane and 6 ml of dichloroethane. To the resultant mixture was added 10 mol % of scandium tris-[tris(C10)methide] (as a Lewis acid catalyst), based on the molar amount of the anisole, thereby obtaining a Lewis acid catalyst composition containing the anisole and the acetic anhydride. The obtained Lewis acid catalyst composition containing the anisole and the acetic anhydride was stirred to thereby perform a reaction between the anisole and the acetic anhydride at 60° C. for 6 hours. Then, the stirred reaction mixture was cooled to room temperature and the cooled reaction mixture was allowed to stand still at room temperature, wherein the reaction mixture rapidly separated into two phases (upper dichloroethane phase and lower perfluoromethylcyclohexane phase) within 10 seconds.

The reaction mixture was analyzed by gas chromatography. It was found that the overall yield of the reaction product (i.e., p-methoxyacetophenone) in the upper and lower phases was 95%. Subsequently, the upper dichloroethane phase containing the product was removed from the reaction mixture and, then, 6 ml of dichloroethane, 216 mg of anisole and 480 mg of acetic anhydride were added to the remainder of the reaction mixture (i.e., perfluoromethylcyclohexane containing the catalyst) to obtain a mixture. Then, the mixture was stirred to thereby perform a reaction at 60° C. for 7 hours. Then, the stirred reaction mixture was allowed to stand still at room temperature, so that the reaction mixture separated into an upper phase and a lower phase. The reaction mixture was analyzed by gas chromatography. It was found that the overall yield of the reaction product (i.e., p-methoxyacetophenone) in the upper and lower phases was 95%.

EXAMPLE 18

1 mmol of adamantanone and 1 mmol of a 33% by weight aqueous hydrogen peroxide were added to a mixed medium of 1.5 ml of perfluoromethylcyclohexane and 1.5 ml of dichloroethane. To the resultant mixture was added 1 mol % of tin tetrakis[bis(C10)imide] (as a Lewis acid catalyst), based on the molar amount of the adamantanone, thereby obtaining a Lewis acid catalyst composition containing the adamantanone and the aqueous hydrogen peroxide. The obtained Lewis acid catalyst composition containing the adamantanone and the aqueous hydrogen peroxide was stirred to thereby perform a reaction for producing a lactone (corresponding to the adamantanone) at 25° C. for 1 hour. The resultant reaction mixture was allowed to stand still, so that the reaction mixture separated into an upper dichloroethane phase and a lower perfluoromethylcyclohexane phase. The upper dichloroethane phase was analyzed by gas chromatography. As a result, it was found that the yield of and selectivity for the reaction product (i.e., a lactone corresponding to the adamantanone) were 89% and 98%, respectively. Subsequently, the amounts of tin tetrakis[bis(C10)imide] present in the upper phase and lower phase were individually measured in terms of the amounts of tin by plasma emission spectrometry. It was found that not less than 99% of the Lewis acid catalyst was present in the lower perfluoromethylcyclohexane phase.

EXAMPLE 19

1 mmol of adamantanone and 0.5 mmol of a 33% by weight aqueous hydrogen peroxide were added to a mixed medium of 2.0 ml of perfluorooctane and 1.5 ml of dichloroethane. To the resultant mixture was added 1 mol % of tin tetrakis[tris(C10)methide] (as a Lewis acid catalyst), based on the molar amount of the adamantanone, thereby obtaining a Lewis acid catalyst composition containing the adamantanone and the aqueous hydrogen peroxide. The obtained Lewis acid catalyst composition containing the adamantanone and the aqueous hydrogen peroxide was stirred to thereby perform a reaction for producing a lactone (corresponding to the adamantanone) at 25° C. for 40 minutes. The resultant reaction mixture was allowed to stand still, so that the reaction mixture separated into an upper dichloroethane phase and a lower perfluorooctane phase. The upper dichloroethane phase was analyzed by gas chromatography. As a result, it was found that the yield of and selectivity for the reaction product (i.e., a lactone corresponding to the adamantanone) were 50% and 100%, respectively. Subsequently, the amounts of tin tetrakis[tris(C10)methide] present in the upper phase and the lower phase were individually measured in terms of the amounts of tin by plasma emission spectrometry. It was found that not less than 99% of the Lewis acid catalyst was present in the lower perfluorooctane phase.

EXAMPLE 20

1 mmol of cyclohexanone and 0.6 mmol of a 33% by weight aqueous hydrogen peroxide were added to a mixed medium of 2.0 ml of perfluoromethylcyclohexane and 1.0 ml of dioxane. To the resultant mixture was added 1 mol % of tin tetrakis[bis(C10)imide] (as a Lewis acid catalyst), based on the molar amount of the cyclohexanone, thereby obtaining a Lewis acid catalyst composition containing the cyclohexanone and the aqueous hydrogen peroxide. The obtained Lewis acid catalyst composition containing the cyclohexanone and the aqueous hydrogen peroxide was stirred to thereby perform a reaction for producing ε-caprolactone at 25° C. for 40 minutes. The resultant reaction mixture was allowed to stand still, so that the reaction mixture separated into an upper dioxane phase and a lower perfluoromethylcyclohexane phase. The upper dioxane phase was analyzed by gas chromatography. As a result, it was found that the yield of and the selectivity for the reaction product (i.e., ε-caprolactone) were 53% and 100%, respectively. Subsequently, the amounts of tin tetrakis[bis(C10)imide] present in the upper phase and the lower phase were individually measured in terms of the amounts of tin by plasma emission spectrometry. It was found that not less than 99% of the Lewis acid catalyst was present in the lower perfluoromethylcyclohexane phase.

EXAMPLE 21

1 mmol of cyclohexanone and 0.6 mmol of a 33% by weight aqueous hydrogen peroxide were added to a mixed medium of 2.0 ml of perfluoromethylcyclohexane and 1.0 ml of dioxane. To the resultant mixture was added 1 mol % of tin tetrakis[bis(C10*,10)imide] (as a Lewis acid catalyst), based on the molar amount of the cyclohexanone, thereby obtaining a Lewis acid catalyst composition containing the cyclohexanone and the aqueous hydrogen peroxide. The obtained Lewis acid catalyst composition containing the cyclohexanone and the aqueous hydrogen peroxide was stirred to thereby perform a reaction for producing ε-caprolactone at 25° C. for 40 minutes. The resultant reaction mixture was allowed to stand still, so that the reaction mixture separated into an upper dioxane phase and a lower perfluoromethylcyclohexane phase. The upper dioxane phase was analyzed by gas chromatography. As a result, it was found that the yield of and selectivity for the reaction product (i.e., ε-caprolactone) were 53% and 100%, respectively. Subsequently, the upper dioxane phase containing the product was removed from the reaction mixture and, then, 1 mmol of cyclohexanone, 0.6 mmol of a 33% by weight aqueous hydrogen peroxide and 1.0 ml of dioxane were added to the remainder of the reaction mixture (i.e., perfluoromethylcyclohexane containing the catalyst) to obtain a mixture. Then, the mixture was stirred to thereby perform a reaction at 25° C. for 40 minutes. Then, the stirred reaction mixture was allowed to stand still at room temperature, so that the reaction mixture separated into an upper phase and a lower phase. The upper phase was analyzed by gas chromatography. As a result, it was found that the yield of and selectivity for the reaction product (i.e., ε-caprolactone) were 54% and 100%, respectively. Substantially the same procedure as mentioned above was repeated further twice. The yields of the produced ε-caprolactone in the twice-repeated reactions were 53% and 52%, respectively, and the selectivities were 100% in both of the twice repeated reactions.

From the above, it was confirmed that when the reaction is performed using the Lewis acid catalyst composition of the present invention, the Lewis acid catalyst can be recycled without suffering the lowering of the catalytic activity.

EXAMPLE 22

1 mmol of adamantanone and 0.8 mmol of a 33% by weight aqueous hydrogen peroxide were added to a mixed medium of 2.0 ml of perfluoromethylcyclohexane and 1.0 ml of dichloroethane. To the resultant mixture was added 1 mol % of tin tetrakis[bis(C10)imide] (as a Lewis acid catalyst), based on the molar amount of the adamantanone, thereby obtaining a Lewis acid catalyst composition containing the adamantanone and the aqueous hydrogen peroxide. The obtained Lewis acid catalyst composition containing the adamantanone and the aqueous hydrogen peroxide was stirred to thereby perform a reaction for producing a lactone (corresponding to the adamantanone) at 25° C. for 40 minutes. The resultant reaction mixture was allowed to stand still, so that the reaction mixture separated into an upper dichloroethane phase and a lower perfluoromethylcyclohexane phase. The upper dichloroethane phase was analyzed by gas chromatography. As a result, it was found that the yield of and selectivity for the reaction product (i.e., a lactone corresponding to the adamantanone) were 77% and 97%, respectively. Subsequently, the upper dichloroethane phase containing the product was removed from the reaction mixture and, then, 1 mmol of adamantanone, 0.8 mmol of a 33% by weight aqueous hydrogen peroxide and 1.0 ml of dichloroethane were added to the remainder of the reaction mixture (i.e., perfluoromethylcyclohexane containing the catalyst) to obtain a mixture. Then, the mixture was stirred to thereby perform a reaction at 25° C. for 1 hour. Then, the stirred reaction mixture was allowed to stand still at room temperature, so that the reaction mixture separated into an upper dichloroethane phase and a lower perfluoromethylcyclohexane phase. The upper dichloroethane phase was analyzed by gas chromatography. As a result, it was found that the yield of and selectivity for the reaction product (i.e., a lactone corresponding to the adamantanone) were 76% and 98%, respectively. Substantially the same procedure as mentioned above was repeated further twice. In each of the twice-repeated reactions, the yield of and the selectivity for the produced lactone were 77% and 98%, respectively. From the above, it was confirmed that when the reaction is performed using the Lewis acid catalyst composition of the present invention, the Lewis acid catalyst can be recycled without suffering the lowering of the catalytic activity.

EXAMPLE 23

1 mmol of dibutyl ketone and 1.1 mmol of a 33% by weight aqueous hydrogen peroxide were added to a mixed medium of 2.0 ml of perfluoromethylcyclohexane and 1.0 ml of dichloroethane. To the resultant mixture was added 2.0 mol % of tin tetrakis[bis(C10)imide] (as a Lewis acid catalyst), based on the molar amount of the dibutyl ketone, thereby obtaining a Lewis acid catalyst composition containing the dibutyl ketone and the aqueous hydrogen peroxide. The obtained Lewis acid catalyst composition containing the dibutyl ketone and the aqueous hydrogen peroxide was stirred to thereby perform a reaction at 80° C. for 4 hours. Then, the stirred reaction mixture was allowed to stand still at room temperature so that the reaction mixture separated into an upper dichloroethane phase and a lower perfluoromethylcyclohexane phase. The upper dichloroethane phase was analyzed by gas chromatography. As a result, it was found that the yield of and selectivity for the reaction product (i.e., an ester corresponding to dibutyl ketone) were 76% and 98%, respectively.

EXAMPLE 24

2 mmol of methyl butyrate and 2 mmol of octanol were added to a mixed medium of 3 ml of perfluorodecalin and 1.0 ml of toluene. To the resultant mixture was added 3 mol % of tin tetrakis[bis(C10)imide] (as a Lewis acid catalyst), thereby obtaining a Lewis acid catalyst composition containing the methyl butyrate and the octanol. The obtained Lewis acid catalyst composition containing the methyl butyrate and the octanol was stirred to thereby perform a reaction at 80° C. for 10 hours. Then, the stirred reaction mixture was allowed to stand still, so that the reaction mixture separated into an upper toluene phase and a lower perfluorodecalin phase. The upper toluene phase was analyzed by gas chromatography. As a result, it was found that the yield of the reaction product (i.e., octyl butyrate) was 91%. Subsequently, the amount of tin tetrakis[bis(C10) imide] present in the lower perfluorodecalin phase was measured in terms of the amount of tin by plasma emission spectrometry. It was found that not less than 99% of the Lewis acid catalyst was present in the lower perfluorodecalin phase.

Comparative Example 8

A reaction was performed in substantially the same manner as in Example 24, except that 3 mol % of tin(IV) chloride was used as the Lewis acid catalyst. The resultant reaction mixture was allowed to stand still, so that the reaction mixture separated into an upper toluene phase and a lower perfluorodecalin phase. The upper toluene phase was analyzed by gas chromatography. As a result, it was found that the yield of the reaction product (i.e., octyl-butyrate) was only 8%.

EXAMPLE 25

2 mmol of methyl butyrate and 2 mmol of octanol were added to a mixed medium of 3 ml of perfluorodecalin and 1 ml of toluene. To the resultant mixture was added 3 mol % of tin tetrakis[bis(C10)imide] (as a Lewis acid catalyst), thereby obtaining a Lewis acid catalyst composition containing the methyl butyrate and the octanol. The obtained Lewis acid catalyst composition containing the methyl butyrate and the octanol was stirred to thereby perform a reaction at 80° C. for 10 hours. The resultant reaction mixture was allowed to stand still, so that the reaction mixture separated into an upper toluene phase and a lower perfluorodecalin phase. The upper toluene phase was analyzed by gas chromatography. As a result, it was found that the yield of the reaction product (i.e., octyl butyrate) was 91%. Subsequently, the upper toluene phase containing the product was removed from the reaction mixture and, then, 2 mmol of methyl dibutylate, 2 mmol of octanol and 1 ml of toluene were added to the remainder of the reaction mixture (i.e., perfluorodecalin containing the catalyst) to obtain a mixture. Then, the mixture was stirred to thereby perform a reaction at 80° C. for 10 hours. Then, the stirred reaction mixture was allowed to stand still at room temperature, so that the reaction mixture separated into an upper toluene phase and a lower perfluorodecalin phase. The upper toluene phase was analyzed by gas chromatography. As a result, it was found that the yield of the reaction product (i.e., octyl butyrate) was 92%. Substantially the same procedure as mentioned above was repeated further twice. In each of the twice-repeated reactions, the yield of the produced octyl butyrate was 91%. From the above, it was confirmed that, when the reaction is performed using the Lewis acid catalyst composition of the present invention, the Lewis acid catalyst can be recycled without suffering the lowering of the catalytic activity even in the presence of water.

EXAMPLE 26

2 mmol of methyl benzoate and 4 mmol of octanol were added to a mixed medium of 3 ml of perfluorodecalin and 1 ml of toluene. To the resultant mixture was added 3 mol % of tin tetrakis[bis(C10)imide] (as a Lewis acid catalyst), thereby obtaining a Lewis acid catalyst composition containing the methyl benzoate and the octanol. The obtained Lewis acid catalyst composition containing the methyl benzoate and the octanol was stirred to thereby perform a reaction at 80° C. for 13 hours. Then, the stirred reaction mixture was allowed to stand still, so that the reaction mixture separated into an upper toluene phase and a lower perfluorodecalin phase. The upper toluene phase was analyzed by gas chromatography. As a result, it was found that the yield of the reaction product (i.e., octyl benzoate) was 80%. Subsequently, the amount of tin tetrakis-[bis(C10) imide] present in the lower perfluorodecalin phase was measured in terms of the amount of tin by plasma emission spectrometry. It was found that not less than 99% of the Lewis acid catalyst was present in the lower perfluorodecalin phase.

EXAMPLE 27

2 mmol of methyl cyclohexanecarboxylate and 2 mmol of octanol were added to a mixed medium of 3 ml of perfluorodecalin and 1 ml of toluene. To the resultant mixture was added 3 mol % of tin tetrakis[bis(C10)imide] (as a Lewis acid catalyst), thereby obtaining a Lewis acid catalyst composition containing the methyl cyclohexanecarboxylate and the octanol. The obtained Lewis acid catalyst composition containing the methyl cyclohexanecarboxylate and the octanol was stirred to thereby perform a reaction at 80° C. for 11 hours. Then, the stirred reaction mixture was allowed to stand still, so that the reaction mixture separated into an upper toluene phase and a lower perfluorodecalin phase. The upper toluene phase was analyzed by gas chromatography. As a result, it was found that the yield of the reaction product (i.e., octyl cyclohexanecarboxylate) was 85%. Subsequently, the amount of tin tetrakis[bis(C10)imide] present in the lower perfluorodecalin phase was measured in terms of the amount of tin by plasma emission spectrometry. It was found that not less than 99% of the Lewis acid catalyst was present in the lower perfluorodecalin phase.

EXAMPLE 28

1 mmol of cyclohexanol and 1 mmol of acetic acid were added to a mixed medium of 3 ml of perfluoromethylcyclohexane and 3 ml of dichloroethane. To the resultant mixture was added 5 mol % of hafnium tetrakis[bis(C10)imide] (as a Lewis acid catalyst), thereby obtaining a Lewis acid catalyst composition containing the cyclohexanol and the acetic acid. The obtained Lewis acid catalyst composition containing the cyclohexanol and the acetic acid was stirred to thereby perform a reaction between the cyclohexanol and the acetic acid at 50° C. for 6 hours. Then, the stirred reaction mixture was allowed to stand still at room temperature, so as to separate the reaction mixture into an upper dichloroethane phase and a lower perfluoromethylcyclohexane phase. The upper dichloroethane phase was analyzed by gas chromatography. As a result, it was found that the yield of the reaction product (i.e., cyclohexyl acetate) was 85%. Subsequently, the amount of hafnium tetrakis[bis(C10) imide] present in the lower perfluoromethylcyclohexane phase was measured in terms of the amount of hafnium by plasma emission spectrometry. It was found that not less than 99% of the Lewis acid catalyst was present in the lower perfluoromethylcyclohexane phase.

From the above, it was confirmed that when the reaction is performed using the Lewis acid catalyst composition of the present invention, the Lewis acid catalyst not only exhibits high catalytic activity even in the presence of water, but also becomes immobilized in the perfluoromethylcyclohexane phase.

EXAMPLE 29

1 mmol of cyclohexanol and 1 mmol of acetic acid were added to a mixed medium of 3 ml of perfluorooctane and 3 ml of toluene. To the resultant mixture was added 3 mol % of hafnium tetrakis[tris(C10)methide] (as a Lewis acid catalyst), thereby obtaining a Lewis acid catalyst composition containing the cyclohexanol and the acetic acid. The obtained Lewis acid catalyst composition containing the cyclohexanol and the acetic acid was stirred to thereby perform a reaction between the cyclohexanol and the acetic acid at 50° C. for 6 hours. Then, the stirred reaction mixture was allowed to stand still at room temperature, so as to separate the reaction mixture into an upper toluene phase and a lower perfluorooctane phase. The upper toluene phase was analyzed by gas chromatography. As a result, it was found that the yield of the reaction product (i.e., cyclohexyl acetate) was 85%. Subsequently, the amount of hafnium tetrakis[tris(C10)methide] present in the lower perfluorooctane phase was measured in terms of the amount of hafnium by plasma emission spectrometry. It was found that not less than 99% of the Lewis acid catalyst was present in the perfluorooctane phase.

From the above, it was confirmed that when the reaction is performed using the Lewis acid catalyst composition of the present invention, the Lewis acid catalyst not only exhibits high catalytic activity even in the presence of water, but also becomes immobilized in the perfluorooctane phase.

EXAMPLE 30

2 mmol of methacrylic acid and 3 mmol of methanol were added to a mixed medium of 5 ml of perfluoromethylcyclohexane and 5 ml of dichloroethane. To the resultant mixture was added 5 mol % of hafnium tetrakis[bis(C10)imide] (as a Lewis acid catalyst), thereby obtaining a Lewis acid catalyst composition containing the methacrylic acid and the methanol. The obtained Lewis acid catalyst composition containing the methacrylic acid and the methanol was stirred to thereby perform a reaction between the methacrylic acid and the methanol at 60° C. for 6 hours. Then, the stirred reaction mixture was allowed to stand still at room temperature, so as to separate the reaction mixture into an upper dichloroethane phase and a lower perfluoromethylcyclohexane phase. The upper dichloroethane phase was analyzed by gas chromatography. As a result, it was found that the yield of the reaction product (i.e., methyl methacrylate) was 87%. Subsequently, the amount of hafnium tetrakis[bis(C10) imide] present in the lower perfluoromethylcyclohexane phase was measured in terms of the amount of hafnium by plasma emission spectrometry. It was found that not less than 99% of the Lewis acid catalyst was present in the lower perfluoromethylcyclohexane phase.

From the above, it was confirmed that when the reaction is performed using the Lewis acid catalyst composition of the present invention, the Lewis acid catalyst not only exhibits high catalytic activity even in the presence of water, but also becomes immobilized in the perfluoromethylcyclohexane phase.

EXAMPLE 31

2 mmol of adamantanone and 1 mmol of a 35% by weight aqueous hydrogen peroxide were added to a mixed medium of 3 ml of perfluoromethylcyclohexane and 3 ml of dichloroethane. To the resultant mixture was added 1 mol % of hafnium tetrakis[bis(C10)imide] (as a Lewis acid catalyst), thereby obtaining a Lewis acid catalyst composition containing the adamantanone and the aqueous hydrogen peroxide. The obtained Lewis acid catalyst composition containing the adamantanone and the aqueous hydrogen peroxide was stirred to thereby perform a reaction for producing a lactone at 25° C. for 30 minutes. Then, the stirred reaction mixture was allowed to stand still at room temperature, so as to separate the reaction mixture into an upper dichloroethane phase and a lower perfluoromethylcyclohexane phase. The upper dichloroethane phase was analyzed by gas chromatography. As a result, it was found that the yield of the reaction product (i.e., a lactone corresponding to the adamantanone) was 93%. Subsequently, the amount of hafnium tetrakis[bis(C10)imide] present in the lower perfluoromethylcyclohexane phase was measured in terms of the amount of hafnium by plasma emission spectrometry. It was found that not less than 99% of the Lewis acid catalyst was present in the lower perfluoromethylcyclohexane phase.

From the above, it was confirmed that when the reaction is performed using the Lewis acid catalyst composition of the present invention, the Lewis acid catalyst not only exhibits high catalytic activity even in the presence of water, but also becomes immobilized in the perfluoromethylcyclohexane phase.

EXAMPLE 32

1 mmol of cyclohexanol and 1 mmol of acetic acid were added to a mixed medium of 3 ml of perfluoromethylcyclohexane and 3 ml of dichloroethane. To the resultant mixture was added 5 mol % of hafnium tetrakis[bis(C10)imide] (as a Lewis acid catalyst), thereby obtaining a Lewis acid catalyst composition containing the cyclohexanol and the acetic acid. The obtained Lewis acid catalyst composition containing the cyclohexanol and the acetic acid was stirred to thereby perform a reaction between the cyclohexanol and the acetic acid at 50° C. for 6 hours. Then, the stirred reaction mixture was allowed to stand still at room temperature, so as to separate the reaction mixture into an upper dichloroethane phase and a lower perfluoromethylcyclohexane phase. The upper dichloroethane phase was analyzed by gas chromatography. As a result, it was found that the yield of the reaction product (i.e., cyclohexyl acetate) was 85%.

Subsequently, the upper dichloroethane phase containing the product was removed from the reaction mixture and, then, 1 mmol of cyclohexanol, 1 mmol of acetic acid and 3 ml of dichloroethane were added to the remainder of the reaction mixture (i.e., perfluoromethylcyclohexane containing the catalyst) to obtain a mixture. Then, the mixture was stirred to thereby perform a reaction at 50° C. for 6 hours. Then, the stirred reaction mixture was allowed to stand still at room temperature, so that the reaction mixture separated into an upper dichloroethane phase and a lower perfluoromethylcyclohexane phase. The upper dichloroethane phase was analyzed by gas chromatography. As a result, it was found that the yield of the reaction product (i.e., cyclohexyl acetate) was 83%.

Substantially the same procedure as mentioned above was repeated further thrice. The yields of the reaction product (i.e., cyclohexyl acetate) in the thrice-repeated reactions were 85%, 84% and 86%, respectively. From the above, it was confirmed that when the reaction is performed using the Lewis acid catalyst composition of the present invention, the catalytic reaction can be performed without suffering the lowering of the catalytic activity even in the presence of water, and the catalyst can be easily recovered and recycled from the reaction mixture.

EXAMPLE 33

2 mmol of adamantanone and 1 mmol of a 35% by weight aqueous hydrogen peroxide were added to a mixed medium of 3 ml of perfluoromethylcyclohexane and 3 ml of dichloroethane. To the resultant mixture was added 1 mol % of hafnium tetrakis[bis(C10)imide] (as a Lewis acid catalyst), based on the molar amount of adamantanone, thereby obtaining a Lewis acid catalyst composition containing the adamantanone and the aqueous hydrogen peroxide. The obtained Lewis acid catalyst composition containing adamantanone and the aqueous hydrogen peroxide was stirred to thereby perform a reaction for producing a lactone (corresponding to the adamantanone) at 25° C. for 30 minutes. The resultant reaction mixture was allowed to stand still, so that the reaction mixture separated into an upper dichloroethane phase and a lower perfluoromethylcyclohexane phase. The upper dichloroethane phase was analyzed by gas chromatography. As a result, it was found that the yield of the reaction product (i.e., a lactone corresponding to the adamantanone) was 91%, based on the amount of hydrogen peroxide used.

The upper dichloroethane phase was removed from the reaction mixture and, then, 2 mmol of adamantanone, 1 mmol of a 35% by weight aqueous hydrogen peroxide and 3 ml of dichloroethane were added to the remainder of the reaction mixture (i.e., perfluoromethylcyclohexane containing the catalyst) to obtain a mixture. Then, the mixture was stirred to thereby perform a reaction for producing a lactone (corresponding to the adamantanone) at 25° C. for 1 hour. Then, the stirred reaction mixture was allowed to stand still, so that the reaction mixture separated into an upper dichloroethane phase and a lower perfluoromethylcyclohexane phase. The upper dichloroethane phase was analyzed by gas chromatography. As a result, it was found that the yield of the lactone was 92%. Substantially the same procedure as mentioned above was repeated further twice. The yields of the lactone in the twice-repeated reactions were 91% and 91%, respectively.

From the above, it was confirmed that when the reaction is performed using the Lewis acid catalyst composition of the present invention, the acid-catalyzed reaction can be performed without suffering the lowering of the catalytic activity even in the presence of water, and the catalyst can be easily recovered and recycled from the reaction mixture.

EXAMPLE 34

166 mg of 2,3-dimethylbutadiene and 200 mg of methyl vinyl ketone were added to a mixed medium of 4 ml of perfluoromethylcyclohexane and 3 ml of dichloroethane. To the resultant mixture was added 3 mol % of hafnium tetrakis[bis(C10)imide] (as a Lewis acid catalyst), thereby obtaining a Lewis acid catalyst composition containing the 2,3-dimethylbutadiene and the methyl vinyl ketone. The obtained Lewis acid catalyst composition containing the 2,3-dimethylbutadiene and the methyl vinyl ketone was stirred to thereby perform a reaction between the 2,3-dimethylbutadiene and the methyl vinyl ketone at 30° C. for 1 hour. Then, the stirred reaction mixture was allowed to stand still at room temperature, so as to separate the reaction mixture into an upper dichloroethane phase and a lower perfluoromethylcyclohexane phase. The upper dichloroethane phase was analyzed by gas chromatography. As a result, it was found that the yield of the reaction product (i.e., 4-acetyl-1,2-dimethylcyclohexene) was 90%. Subsequently, the amount of hafnium tetrakis[bis(C10)imide] present in the lower perfluoromethylcyclohexane phase was measured in terms of the amount of hafnium by plasma emission spectrometry. It was found that not less than 99% of the Lewis acid catalyst was present in the lower perfluoromethylcyclohexane phase.

EXAMPLE 35

Two glass tubes (first and second glass tubes, each having an inner diameter of 7 mm) were connected to a reaction vessel (internal volume: 70 ml), wherein the first glass tube was connected to a portion which is 10 mm below the top of the reaction vessel and the second glass tube was connected to a portion which is 10 mm above the bottom of the reaction vessel, and a 10 ml decanter (as a phase separator) was connected to the reaction vessel through the two glass tubes. 25 ml of perfluoromethylcyclohexane and 0.25 mmol of ytterbium tris[bis(C10)imide] (as a Lewis acid catalyst) were charged into the reaction vessel. Then, 300 ml of a toluene solution containing 0.51 mol of cyclohexanol and 0.56 mol of acetic anhydride was introduced into the reaction vessel from the bottom portion thereof at a flow rate of 23 ml/hour by using a feed pump, while agitating the resultant mixture vigorously to thereby perform a reaction therebetween. The temperature of the reaction vessel was maintained at room temperature and the reaction was continuously performed for 100 hours. During the reaction, a part of the reaction mixture was withdrawn from the reaction vessel and introduced into the decanter through the first glass tube. In the decanter, the reaction mixture was separated into an upper toluene phase containing the desired reaction product and a lower perfluoromethylcyclohexane phase containing the Lewis acid catalyst, and the upper toluene phase containing the reaction product was continuously separated and recovered from the upper portion of the decanter, while withdrawing the lower perfluoromethylcyclohexane phase containing the Lewis acid catalyst from the bottom portion of the decanter and recycling it into the reaction vessel through the second glass tube.

The recovered toluene phase was analyzed by gas chromatography. As a result, it was found that the yield of the desired reaction product (i.e., cyclohexyl acetate) was not less than 98% even at the point in time of 100 hours after the start of the reaction. The amount of ytterbium tris[bis(C10) imide] (Lewis acid catalyst) present in the toluene phase was measured in terms of the amount of ytterbium by plasma emission spectrometry, and was found to be not more than 1 ppm.

In the above-mentioned continuous reaction, the migration of the catalyst into the toluene phase containing the product did not occur, which migration leads to the loss of the catalyst. Further, the catalytic activity of the catalyst did not become lowered during the reaction performed continuously for 100 hours.

EXAMPLE 36

Two glass tubes (first and second glass tubes, each having an inner diameter of 7 mm) were connected to a reaction vessel (internal volume: 70 ml), wherein the first glass tube was connected to a portion which is 10 mm below the top of the reaction vessel and the second glass tube was connected to a portion which is 10 mm above the bottom of the reaction vessel, and a 10 ml decanter (as a phase separator) was connected to the reaction vessel through the two glass tubes. 25 ml of perfluoromethylcyclohexane and 0.25 mmol of hafnium tetrakis[bis(C10*,10)imide] (as a Lewis acid catalyst) were charged into the reaction vessel. Then, 300 ml of a toluene solution containing 0.51 mol of cyclohexanol and 0.56 mol of acetic anhydride was introduced into the reaction vessel from the bottom portion thereof at a flow rate of 40 ml/hour by using a feed pump, while agitating the resultant mixture vigorously to thereby perform a reaction therebetween. The temperature of the reaction vessel was maintained at room temperature and the reaction was continuously performed for 100 hours. During the reaction, a part of the reaction mixture was withdrawn from the reaction vessel and introduced into the decanter through the first glass tube. In the decanter, the reaction mixture was separated into an upper toluene phase containing the desired reaction product and a lower perfluoromethylcyclohexane phase containing the Lewis acid catalyst, and the upper toluene phase containing the reaction product was continuously separated and recovered from the upper portion of the decanter, while withdrawing the lower perfluoromethylcyclohexane phase containing the Lewis acid catalyst from the bottom portion of the decanter and recycling it into the reaction vessel through the second glass tube. The recovered toluene phase was analyzed by gas chromatography. As a result, it was found that the yield of the desired reaction product (i.e., cyclohexyl acetate) was not less than 98% even at the point in time of 100 hours after the start of the reaction. The amount of hafnium tris[bis(C10*,10)imide] (Lewis acid catalyst) present in the toluene phase was measured in terms of the amount of hafnium by plasma emission spectrometry, and was found to be not more than 1 ppm.

In the above-mentioned continuous reaction, the migration of the catalyst into the toluene phase containing the product did not occur, which migration leads to the loss of the catalyst. Further, the catalytic activity of the catalyst did not become lowered.

EXAMPLE 37

A partition plate was attached to the inside of a vertical reaction column (diameter: 20 mm, height: 85 mm) at a position which is 20 mm below the column top, such that a gap is formed between the partition plate and the inner wall of the column. Into the reaction column was charged 4 ml of perfluoromethylcyclohexane and 0.03 mol of scandium tris [bis(C10)imide] (as a Lewis acid catalyst) to thereby form a stationary phase. As a mobile phase, 100 ml of dichloroethane containing 15 mmol of cyclohexanol and 16 mmol of acetic anhydride was charged into the reaction column from the bottom portion thereof at a flow rate of 9 ml/hour by using a feed pump, while stirring the stationary phase at the bottom portion of the column. The temperature of the reaction zone in the reaction column was maintained at 35° C. and the reaction was performed for 100 hours. During the reaction, a part of the upper dichloroethane phase containing a desired reaction product, which part was positioned above the partition plate, was continuously withdrawn from the reaction mixture. The withdrawn dichloroethane phase was analyzed by gas chromatography. It was found that the yield of the desired reaction product (i.e., cyclohexyl acetate) was 99%. The amount of scandium tris[bis(C10)imide] (Lewis acid catalyst) present in the dichloroethane phase was measured in terms of the amount of scandium by plasma emission spectrometry, and was found to be not more than 1 ppm.

EXAMPLE 38

Use was made of a reaction column which is substantially the same as that of Example 37, except that the reaction column was not equipped with a partition plate. Into the reaction column was charged 4 ml of perfluorooctane and 0.03 mmol of scandium tris[bis(C10)imide] (as a Lewis acid catalyst) to thereby form a stationary phase. As a mobile phase, 100 ml of toluene containing 15 mmol of cyclohexanol and 16 mmol of acetic anhydride was charged into the reaction column from the bottom portion thereof at a flow rate of 8 ml/hour by using a feed pump, while stirring the stationary phase at the bottom portion of the column. The temperature of the reaction zone in the reaction column was maintained at 35° C. and the reaction was performed for 100 hours. During the reaction, an upper portion of the reaction mixture, which is the phase-separated, reaction-formed toluene phase containing a desired reaction product, was continuously withdrawn from the reaction mixture. The withdrawn toluene phase was analyzed by gas chromatography. It was found that the yield of the desired reaction product (i.e., cyclohexyl acetate) was 99%. The amount of scandium tris[bis(C10)imide] (Lewis acid catalyst) present in the dichloroethane phase was measured in terms of the amount of scandium by plasma emission spectrometry, and was found to be not more than 1 ppm.

EXAMPLE 39

Use was made of a reaction column equipped with a partition plate, which reaction column was the same as that used in Example 37. Into the reaction column was charged 4 ml of perfluoromethylcyclohexane and 0.03 mmol of scandium tris[bis(C10)imide] (as a Lewis acid catalyst) to thereby form a stationary phase. As a mobile phase, 100 ml of chlorobenzene containing 15 mmol of cyclohexanol and 16 mmol of acetic anhydride was charged into the reaction column from the bottom portion thereof at a flow rate of 8 ml/hour by using a feed pump, while stirring the stationary phase at the bottom portion of the column. The temperature of the reaction zone in the reaction column was maintained at 30° C. and the reaction was performed for 100 hours. During the reaction, a part of the upper chlorobenzene phase containing a desired reaction product, which part was positioned above the partition plate, was continuously withdrawn from the reaction mixture. The withdrawn chlorobenzene phase was analyzed by gas chromatography. It was found that the yield of the desired reaction product (i.e., cyclohexyl acetate) was 98%. The amount of scandium tris[bis(C10)imide] (Lewis acid catalyst) present in the chlorobenzene phase was measured in terms of the amount of scandium by plasma emission spectrometry, and was found to be not more than 1 ppm.

EXAMPLE 40

Use was made of a reaction column equipped with a partition plate, which reaction column was the same as that used in Example 37. Into the reaction column was charged 4 ml of perfluoromethylcyclohexane and 0.03 mmol of hafnium tetrakis[bis(C10)imide] (as a Lewis acid catalyst) to thereby form a stationary phase. As a mobile phase, 100 ml of dichloroethane containing 15 mmol of cyclohexanol and 16 mmol of acetic anhydride was charged into the reaction column from the bottom portion thereof at a flow rate of 12 ml/hour by using a feed pump, while stirring the stationary phase at the bottom portion of the column. The temperature of the reaction zone in the reaction column was maintained at 35° C. and the reaction was performed for 100 hours. During the reaction, a part of the upper dichloroethane phase containing a desired reaction product, which part was positioned above the partition plate, was continuously withdrawn from the reaction mixture. The withdrawn dichloroethane phase was analyzed by gas chromatography. It was found that the yield of the desired reaction product (i.e., cyclohexyl acetate) was 99%. The amount of hafnium tetrakis[bis(C10)imide] (Lewis acid catalyst) present in the dichloroethane phase was measured in terms of the amount of hafnium by plasma emission spectrometry, and was found to be not more than 1 ppm.

EXAMPLE 41

Use was made of a reaction column equipped with a partition plate, which reaction column was the same as that used in Example 37. Into the reaction column was charged 4 ml of perfluoromethylcyclohexane and 0.03 mmol of hafnium tetrakis[bis(C10)imide] (as a Lewis acid catalyst) to thereby form a stationary phase. As a mobile phase, 100 ml of dichloroethane containing 15 mmol of 2,3-methylbutadiene and 18 mmol of acetic anhydride was charged into the reaction column from the bottom portion thereof at a flow rate of 5 ml/hour by using a feed pump, while stirring the stationary phase at the bottom portion of the column. The temperature of the reaction zone in the reaction column was maintained at 40° C. and the reaction was performed for 50 hours. During the reaction, a part of the upper dichloroethane phase was containing a desired reaction product, which part was positioned above the partition plate, was continuously withdrawn from the reaction mixture. The withdrawn dioxane phase was analyzed by gas chromatography. It was found that the yield of the desired reaction product (i.e., 4-acetyl-1,2-dimethylcyclohexene) was 76%. The amount of hafnium by plasma emission spectrometry, and was found to be not more than 1 ppm.

EXAMPLE 42

Use was made of a reaction column equipped with a partition plate, which reaction column was the same as that used in Example 37. Into the reaction column was charged 4 ml of perfluorooctane and 0.03 mmol of hafnium tetrakis [bis(C10)imide] (as a Lewis acid catalyst) to thereby form a stationary phase. As a mobile phase, 100 ml of dichloroethane containing 15 mmol of 2,3-methylbutadiene and 18 mmol of acetic anhydride was charged into the reaction column from the bottom portion thereof at a flow rate of 5 ml/hour by using a feed pump, while stirring the stationary phase at the bottom portion of the column. The temperature of the reaction zone in the reaction column was maintained at 40° C. and the reaction was performed for 50 hours. During the reaction, a part of the upper dichloroethane phase containing a desired reaction product, which part was positioned above the partition plate, was continuously withdrawn from the reaction mixture. The withdrawn dichloroethane phase was analyzed by gas chromatography. It was found that the yield of the desired reaction product (i.e., 5-acetyl-2,3-dimethyl-cyclohexa-2-ene) was 76%. The amount of hafnium tetrakis-[bis(C10)imide] (Lewis acid catalyst) present in the dichloroethane phase was measured in terms of the amount of hafnium by plasma emission spectrometry, and was found to be not more than 1 ppm.

EXAMPLE 43

Into a 50 ml-reaction vessel was charged 4 ml of perfluorooctane and 0.05 mmol of ytterbium tris[bis(C10)imide] (as a Lewis acid catalyst) to thereby form a stationary phase. As a mobile phase, 100 ml of dichloroethane containing 15 mmol of 2,3-dimethylbutadiene and 18 mmol of methyl vinyl ketone was charged into the reaction vessel at a flow rate of 5 ml/hour by using a feed pump, while stirring the stationary phase at the bottom portion of the reaction vessel. The temperature of the reaction zone in the reaction vessel was maintained at 35° C. and the reaction was performed for 40 hours. During the reaction, an upper portion of the reaction mixture, which is the phase-separated, reaction-formed dichloroethane phase containing a desired reaction product, was continuously withdrawn from the reaction vessel. The withdrawn dichloroethane phase was analyzed by gas chromatography. It was found that the yield of the desired reaction product (i.e., 4-acetyl-1,2-dimethylcyclohexene) was 75%. The amount of ytterbium tris[bis(C10) imide] (Lewis acid catalyst) in the dichloroethane phase was measured in terms of the amount of ytterbium by plasma emission spectrometry, and was found to be not more than 1 ppm.

EXAMPLE 44

A static mixer (inner diameter: 15 mm, length: 300 mm) provided with a jacket was used as a pipe reactor. The static mixer (as a pipe reactor) was simultaneously charged with 500 ml of perfluorooctane containing 0.5 mmol of scandium tris[bis(C10)imide] (as a Lewis acid catalyst) and 500 ml of dioxane containing 100 mmol of cyclohexanol and 200 mmol of acetic anhydride, wherein the perfluorooctane and the dioxane were individually fed to the pipe reactor at a flow rate of 30 ml/hour by using feed pumps, to thereby perform a reaction between the cyclohexanol and the acetic anhydride. A heated water at about 35° C. was circulated in the jacket so as to heat the pipe reactor. During the reaction, a part of the reaction mixture which flowed out from the pipe reactor was continuously introduced into a phase separation vessel and subjected to phase separation, thereby obtaining a reaction-formed upper dioxane phase containing unreacted reactants and a desired reaction product and a reaction-formed lower perfluorooctane phase containing the catalyst. The lower perfluorooctane phase containing the catalyst was returned to the pipe reactor. The upper dioxane phase was withdrawn from the phase separation vessel and analyzed by gas chromatography. When the amount of the desired reaction product (i.e., cyclohexyl acetate) contained in the dioxane phase was lower than the predetermined amount, the dioxane phase was returned to the pipe reactor so as to perform the reaction using the unreacted reactants contained therein. The final yield of the product was 99%.

EXAMPLE 45

A reaction was performed in substantially the same manner as in Example 24, except that 3 mol % of tin tetrakis [tris(C10)methide] was used as the Lewis acid catalyst. The resultant reaction mixture was allowed to stand still at room temperature, so that the reaction mixture separated into an upper toluene phase and a lower perfluorodecalin phase. The upper toluene phase was analyzed by gas chromatography. It was found that the yield of the reaction product (i.e., octyl butyrate) was 92%. Subsequently, the amount of tin tetrakis [tris(C10)methide] (Lewis acid catalyst) present in the lower perfluorodecalin phase was measured in terms of the amount of tin by plasma emission spectrometry. It was found that not less than 99% of the Lewis acid catalyst was present in the lower phase.

EXAMPLE 46

Two glass tubes (first and second glass tubes, each having an inner diameter of 7 mm) were connected to a reaction vessel (internal volume: 70 ml), wherein the first glass tube was connected to a portion which is 10 mm below the top of the reaction vessel and the second glass tube was connected to a portion which is 10 mm above the bottom of the reaction vessel, and a 10 ml decanter (as a phase separator) was connected to the reaction vessel through the two glass tubes. 25 ml of perfluoromethylcyclohexane containing 0.25 mmol of scandium tris[tris(C10)methide] (as a Lewis acid catalyst) was charged into the reaction vessel in the same manner as in Example 35. Then, 300 ml of toluene containing 0.51 mol of cyclohexanol and 0.56 mol of acetic anhydride was introduced into the reaction vessel from the bottom portion thereof at a flow rate of 23 ml/hour by using a feed pump, while agitating the resultant mixture vigorously to thereby perform a reaction therebetween. The temperature of the reaction vessel was maintained at room temperature and the reaction was continuously performed for 100 hours. During the reaction, a part of the reaction mixture was withdrawn from the reaction vessel and introduced into the decanter through the first glass tube. In the decanter, the reaction mixture was separated into an upper toluene phase containing the desired reaction product and a lower perfluoromethylcyclohexane phase containing the Lewis acid catalyst, and the upper toluene phase containing the reaction product was continuously separated and recovered from the upper portion of the decanter, while withdrawing the lower perfluoromethylcyclohexane phase containing the Lewis acid catalyst from the bottom portion of the decanter and recycling it into the reaction vessel through the second glass tube. The recovered toluene phase was analyzed by gas chromatography. As a result, it was found that the yield of the desired reaction product (i.e., cyclohexyl acetate) was not less than 99% even at the point in time of 100 hours after the start of the reaction. The amount of scandium tris[tris(C10)methide] (Lewis acid catalyst) present in the toluene phase was measured in terms of the amount of scandium by plasma emission spectrometry, and was found to be not more than 1 ppm.

In the above-mentioned continuous reaction, the migration of the catalyst into the toluene phase containing the product did not occur, which migration leads to the loss of the catalyst. Further, the catalytic activity of the catalyst did not become lowered during the reaction performed continuously for 100 hours.

INDUSTRIAL APPLICABILITY

By the use of the Lewis acid catalyst composition of the present invention for a Lewis acid-catalyzed reaction, after the reaction, not only can the Lewis acid catalyst be easily separated and recovered from the acid-catalyzed reaction mixture containing the same, but also the recycling of the Lewis acid catalyst can be performed without suffering the lowering of the catalytic activity. Further, when a reaction which proceeds in the presence of a Lewis acid catalyst is performed in a continuous manner by the method of the present invention, by virtue of very high phase separation rate of the reaction mixture, the reaction can be easily and simply performed without using complicated apparatuses or without repeating the phase separation operation. In addition, the Lewis acid catalyst of the present invention has high solubility in a fluorinated compound medium and has high catalytic activity as compared to those of the conventional Lewis acid catalysts, so that the Lewis acid catalyst of the present invention can be used advantageously for an acid-catalyzed reaction without suffering the lowering of the catalytic activity.

The invention claimed is:

1. A Lewis acid catalyst composition comprising a mixed medium and a Lewis acid catalyst, said mixed medium comprising (A) a fluorinated compound medium and (B) a non-fluorinated compound medium which can be phase-separated from the fluorinated compound medium (A), said Lewis acid catalyst being at least one compound selected from the group consisting of compounds respectively represented by the following formulae (1) and (2):

$$[(R_f^1SO_2)(R_f^2SO_2)N]_nM \quad (1),$$

and $$[(R_f^1SO_2)(R_f^2SO_2)(R_f^3SO_2)C]_nM \quad (2)$$

wherein:

each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is said substituent ($\alpha$) and, in formula (2) above, at least one member selected from the group consisting of $R_f^1$ to $R_f^3$ is said substituent ($\alpha$), wherein, in said partially substituted derivative in the definition of each of said substituents ($\alpha$) and ($\beta$), a part of the fluorine atoms in said perfluorinated hydrocarbon group is replaced by at least one member selected from the group consisting of a hydrogen atom and a halogen atom exclusive of a fluorine atom, provided that, in each of said substituents ($\alpha$) and ($\beta$), a part of the fluorine atoms bonded to a carbon atom directly bonded to the —SO$_2$ group is not replaced by a hydrogen atom;

M represents an atom selected from the group consisting of transition metals including rare earth metals, gallium, indium, thallium, silicon, germanium, tin, lead, antimony and bismuth; and n is an integer equivalent to the valence of M.

2. The Lewis acid catalyst composition according to claim 1, wherein each of $R_f^1$ to $R_f^3$ in said formulae (1) and (2) independently represents substituent ($\alpha$) which is represented by any one of the following formulae (3) and (4):

$$CF_2X^1CFX^2-[OCF_2CF(CF_3)]_t-O-[CF_2]_u- \quad (3),$$

and $$CF_2=CF-[OCF_2CF(CF_3)]_t-O-[CF_2]_u- \quad (4)$$

wherein, each of $X^1$ and $X^2$ independently represents an atom selected from the group consisting of a halogen atom and a hydrogen atom; t is an integer of from 1 to 4; and u is an integer of from 1 to 4.

3. A method for continuously performing a reaction which proceeds in the presence of a Lewis acid catalyst, which comprises:

providing a reaction zone containing a Lewis acid catalyst and a fluorinated compound medium (A), wherein said Lewis acid catalyst is at least one compound selected from the group consisting of compounds respectively represented by the following formulae (1) and (2):

$$[(R_f^1SO_2)(R_f^2SO_2)N]_nM \quad (1),$$

and $$[(R_f^1SO_2)(R_f^2SO_2)(R_f^3SO_2)C]_nM \quad (2)$$

wherein:

each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (1) above, at least one member selected from the group consisting of $R_f^1$ and $R_f^2$ is said substituent ($\alpha$) and, in formula (2) above, at least one member selected from the group consisting of $R_f^1$ to $R_f^3$ is said substituent ($\alpha$), wherein, in said partially substituted derivative in the definition of each of said substituents ($\alpha$) and ($\beta$), a part of the fluorine atoms in said perfluorinated hydrocarbon group is replaced by at least one member selected from the group consisting of a hydrogen atom and a halogen atom exclusive of a fluorine atom, provided that, in each of said substituents ($\alpha$) and ($\beta$), a part of the fluorine atoms bonded to a carbon atom directly bonded to the —SO$_2$ group is not replaced by a hydrogen atom, M represents an atom selected from the group consisting of transition metals including rare earth metals, gallium, indium, thallium, silicon, germanium, tin, lead, antimony and bismuth, and n is an integer equivalent to the valence of M; and continuously feeding a mixture of at least one reactant and a non-fluorinated compound medium (B) which can be phase-separated from said fluorinated compound medium (A) and mixing said fluorinated compound medium (A) containing said Lewis acid catalyst and said non-fluorinated compound medium (B) containing at least one reactant to thereby effect a reaction in the presence of said Lewis acid catalyst and obtain a reaction mixture comprising said flourinated compound medium (A), said non-fluorinated compound medium (B), said Lewis acid catalyst and a reaction product, while continuously separating said reaction mixture into a reaction-formed non-fluorinated compound medium (B) phase containing said reaction product and a reaction-formed fluorinated compound medium (A) phase containing said Lewis acid catalyst in a phase separation zone which is disposed in association with said reaction zone and while continuously withdrawing said reaction-formed non-fluorinated compound medium (B) phase containing said reaction product from said phase separation zone.

4. The method according to claim 3, wherein M in said formulae (1) and (2) represents tin, and said reaction which proceeds in the presence of a Lewis acid catalyst is selected from the group consisting of an oxidation reaction of a ketone compound by use of hydrogen peroxide and a transesterification reaction.

5. The method according to claim 3, wherein M in said formulae (1) and (2) represents hafnium, and said reaction which proceeds in the presence of a Lewis acid catalyst is selected from the group consisting of a carbon-carbon bond-forming reaction, a dehydration reaction and an oxidation reaction by use of hydrogen peroxide.

6. A Lewis acid catalyst which is a compound represented by the following formula (1'):

$$[(R_f^1SO_2)(R_f^2SO_2)N]_nM \quad (1')$$

wherein:
each of $R_f^1$ and $R_f^2$ independently represents a substituent selected from the group consisting of a perfluorinated, saturated $C_9$–$C_{16}$ hydrocarbon group containing in the skeleton thereof at least one heteroatom selected from the group consisting of a nitrogen atom and an oxygen atom and a partially substituted derivative thereof,
wherein, in said partially substituted derivative in the definition of said substituent, a part of the fluorine atoms in said perfluorinated hydrocarbon group is replaced by at least one member selected from the group consisting of a hydrogen atom and a halogen atom exclusive of a fluorine atom, provided that, in said substituent, a part of the fluorine atoms bonded to said carbon atom directly bonded to the —SO$_2$ group is not replaced by a hydrogen atom;
M represents an atom selected from the group consisting of transition metals including rare earth metals, gallium, indium, thallium, silicon, germanium, tin, lead, antimony and bismuth; and
n is an integer equivalent to the valence of M.

7. The Lewis acid catalyst according to claim 6, wherein each of $R_f^1$ and $R_f^2$ in said formula (1') represents a substituent represented by the following formula (3):

$$CF_2X^1CFX^2\text{—}[OCF_2CF(CF_3)]_t\text{—}O\text{—}[CF_2]_u\text{—} \quad (3)$$

wherein, each of $X^1$ and $X^2$ independently represents an atom selected from the group consisting of a halogen atom and a hydrogen atom; t is an integer of from 1 to 4; and u is an integer of from 1 to 4.

8. The Lewis acid catalyst according to claim 6 or 7, wherein M in said formula (1') represents tin.

9. The Lewis acid catalyst according to claim 6 or 7, wherein M in said formula (1') represents hafnium.

10. A Lewis acid catalyst which is a compound represented by the following formula (2'):

$$[(R_f^1SO_2)(R_f^2SO_2)(R_f^3SO_2)C]_nM \quad (2')$$

wherein:
each of $R_f^1$ to $R_f^3$ in said formula (2') represents a substituent represented by the following formula (3):

$$CF_2X^1CFX^2\text{—}[OCF_2CF(CF_3)]_t\text{—}O\text{—}[CF_2]_u\text{—} \quad (3)$$

wherein, each of $X^1$ and $X^2$ independently represents an atom selected from the group consisting of a halogen atom and a hydrogen atom; t is an integer of from 1 to 4; and u is an integer of from 1 to 4;

M represents an atom selected from the group consisting of transition metals including rare earth metals, gallium, indium, thallium, silicon, germanium, tin, lead, antimony and bismuth; and
n is an integer equivalent to the valence of M.

11. The Lewis acid catalyst according to claim 10, wherein M in said formula (2') represents tin.

12. The Lewis acid catalyst according to claim 10, wherein M in said formula (2') represents hafnium.

13. A Lewis acid catalyst which is at least one compound selected from the group consisting of compounds respectively represented by the following formulae (5) and (6):

$$[(R_f^1SO_2)(R_f^2SO_2)N]_nSn \quad (5),$$

and $$[(R_f^1SO_2)(R_f^2SO_2)(R_f^3SO_2)C]_nSn \quad (6)$$

wherein:
each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (5) above, at least one member selected from the group consisting of $R_f^1$ and $R_f^2$ is said substituent ($\alpha$) and, in formula (6) above, at least one member selected from the group consisting of $R_f^1$ to $R_f^3$ is said substituent ($\alpha$),
wherein, in said partially substituted derivative in the definition of each of said substituents ($\alpha$) and ($\beta$), a part of the fluorine atoms in said perfluorinated hydrocarbon group is replaced by at least one member selected from the group consisting of a hydrogen atom and a halogen atom exclusive of a fluorine atom, provided that, in each of said substituents ($\alpha$) and ($\beta$), a part of the fluorine □atoms bonded to a carbon atom directly bonded to the —SO$_2$ group is not replaced by a hydrogen atom; and
n is an integer equivalent to the valence of Sn.

14. A Lewis acid catalyst which is at least one compound selected from the group consisting of compounds respectively represented by the following formulae (7) and (8):

$$[(R_f^1SO_2)(R_f^2SO_2)N]_nHf \quad (7),$$

and $$[(R_f^1SO_2)(R_f^2SO_2)(R_f^3SO_2)C]_nHf \quad (8)$$

wherein:
each of $R_f^1$ to $R_f^3$ independently represents a substituent ($\alpha$) selected from the group consisting of a perfluorinated, saturated or unsaturated $C_7$–$C_{20}$ hydrocarbon group containing in the skeleton thereof at least one heteroatom selected from the group consisting of a nitrogen atom and an oxygen atom and a partially substituted derivative thereof, or a substituent ($\beta$) selected from the group consisting of a perfluorinated, saturated or unsaturated $C_1$–$C_{16}$ hydrocarbon group containing no heteroatom and a partially substituted derivative thereof, provided that, in formula (7) above, at least one member selected from the group consisting of $R_f^1$ and $R_f^2$ is said substituent (α) and, in formula (8) above, at least one member selected from the group consisting of $R_f^1$ to $R_f^3$ is said substituent (α), wherein, in said partially substituted derivative in the definition of each of said substituents (α) and (β), a part of the fluorine atoms in said perfluorinated hydrocarbon group is replaced by at least one member selected from the group consisting of a hydrogen atom and a halogen atom exclusive of a fluorine atom, provided that, in each of said substituents (α) and (β), a part of the fluorine atoms bonded to a carbon atom directly bonded to the —$SO_2$ group is not replaced by a hydrogen atom; and n is an integer equivalent to the valence of Hf.

* * * * *